(12) United States Patent
Otsu et al.

(10) Patent No.: US 9,581,571 B2
(45) Date of Patent: Feb. 28, 2017

(54) ACOUSTIC SENSOR AND ACOUSTIC SENSOR SYSTEM

(71) Applicant: KABUSHIKI KAISHA TOSHIBA, Tokyo (JP)

(72) Inventors: Kenji Otsu, Tokyo (JP); Hideaki Fukuzawa, Kawasaki Kanagawa (JP); Michiko Hara, Yokohama Kanagawa (JP); Tomio Ono, Yokohama Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 224 days.

(21) Appl. No.: 14/465,300

(22) Filed: Aug. 21, 2014

(65) Prior Publication Data
US 2015/0082888 A1 Mar. 26, 2015

(30) Foreign Application Priority Data

Sep. 20, 2013 (JP) .................................. 2013-196205

(51) Int. Cl.
*G01N 29/14* (2006.01)
*G01N 29/28* (2006.01)
(Continued)

(52) U.S. Cl.
CPC ............. *G01N 29/14* (2013.01); *G01N 29/12* (2013.01); *G01N 29/245* (2013.01); *G01N 29/28* (2013.01);
(Continued)

(58) Field of Classification Search
CPC ........ G01L 9/0042; G01L 9/16; G01L 9/0044; G01L 9/0048; G01L 1/125; G01L 1/12;
(Continued)

(56) References Cited

U.S. PATENT DOCUMENTS 7,490,517 B2 * 2/2009 Yoshida ................. G01D 11/30
73/597
2006/0242852 A1 11/2006 Lin
(Continued)

FOREIGN PATENT DOCUMENTS

JP 11-056834 3/1999
JP 2002-148132 5/2002
(Continued)

*Primary Examiner* — Helen Kwok
(74) *Attorney, Agent, or Firm* — Finnegan, Henderson, Farabow, Garrett & Dunner LLP

(57) ABSTRACT

According to one embodiment, an acoustic sensor includes a base and a first strain sensing element. The base includes a support and a first film unit supported by the support. The first film unit is flexible. The first strain sensing element is provided on a first surface of the first film unit. The first strain sensing element includes a first magnetic layer, a second magnetic layer, and a first intermediate layer provided between the first magnetic layer and the second magnetic layer. An angle between a magnetization of the first magnetic layer and a magnetization of the second magnetic layer is variable by an acoustic wave. The acoustic wave is transmitted to a first film unit by a first transmitting material in contact with the first film unit.

26 Claims, 11 Drawing Sheets

(51) Int. Cl.
*G01N 29/12* (2006.01)
*G01N 29/24* (2006.01)

(52) U.S. Cl.
CPC .............. *G01N 2291/0234* (2013.01); *G01N 2291/0238* (2013.01); *G01N 2291/0258* (2013.01)

(58) Field of Classification Search
CPC ...... H04R 19/04; H04R 19/005; G01N 29/12; G01N 29/245; G01N 29/28; G01N 29/14; G01N 29/36; G01N 29/04
USPC .............................. 73/587, 862.69, 779, 726
See application file for complete search history.

(56) References Cited

U.S. PATENT DOCUMENTS

| | | | |
|---|---|---|---|
| 2007/0079661 A1 | 4/2007 | Yoshida et al. | |
| 2011/0295128 A1 | 12/2011 | Yuasa et al. | |
| 2012/0079887 A1 | 4/2012 | Giddings et al. | |
| 2012/0245477 A1 | 9/2012 | Giddings et al. | |
| 2013/0076687 A1 | 3/2013 | Giddings et al. | |
| 2013/0079648 A1 | 3/2013 | Fukuzawa et al. | |
| 2013/0170669 A1* | 7/2013 | Fukuzawa | G01L 9/0042 381/115 |
| 2013/0255069 A1* | 10/2013 | Higashi | G01R 3/00 29/595 |
| 2013/0255393 A1* | 10/2013 | Fukuzawa | G01L 1/12 73/779 |
| 2014/0069200 A1 | 3/2014 | Yuasa et al. | |
| 2014/0090486 A1* | 4/2014 | Fuji | G01L 9/0044 73/862.69 |
| 2014/0137658 A1* | 5/2014 | Higashi | H04R 19/04 73/779 |
| 2014/0137668 A1* | 5/2014 | Fukuzawa | B81B 3/0086 73/862.69 |
| 2015/0088008 A1* | 3/2015 | Fuji | G01L 9/16 600/485 |

FOREIGN PATENT DOCUMENTS

| | | |
|---|---|---|
| JP | 2005-147711 | 6/2005 |
| JP | 2007-107954 | 4/2007 |
| JP | 2007-319576 | 12/2007 |
| JP | 2009-290293 | 12/2009 |
| JP | 4621913 | 11/2010 |
| JP | 2012-78186 | 4/2012 |
| JP | 2012-150074 | 8/2012 |
| JP | 2012-176294 | 9/2012 |
| JP | 2012-204479 | 10/2012 |
| JP | 5101659 | 10/2012 |
| JP | 2013-70732 | 4/2013 |
| JP | 2013-72712 | 4/2013 |
| JP | 2013-73374 | 4/2013 |
| JP | 2013-165977 | 8/2013 |
| JP | 2013-205255 | 10/2013 |
| JP | 2013-205403 | 10/2013 |
| JP | 2014-52360 | 3/2014 |
| JP | 2014-74606 | 4/2014 |
| JP | 2014-102171 | 6/2014 |
| JP | 2014-103539 | 6/2014 |
| JP | 2014-142323 | 8/2014 |
| JP | 2014-173844 | 9/2014 |

* cited by examiner

US 9,581,571 B2

ACOUSTIC SENSOR AND ACOUSTIC SENSOR SYSTEM

CROSS-REFERENCE TO RELATED APPLICATIONS

This application is based upon and claims the benefit of priority from Japanese Patent Application No. 2013-196205, filed on Sep. 20, 2013; the entire contents of which are incorporated herein by reference.

FIELD

Embodiments described herein relate generally to an acoustic sensor and an acoustic sensor system.

BACKGROUND

Acoustic emission (hereinafter, referred to as "AE") is used as a method for non-destructive testing using an ultrasonic sensor, for example. It is desired for acoustic sensors using such acoustic emission to improve sensitivity.

DETAILED DESCRIPTION

Figure 1:
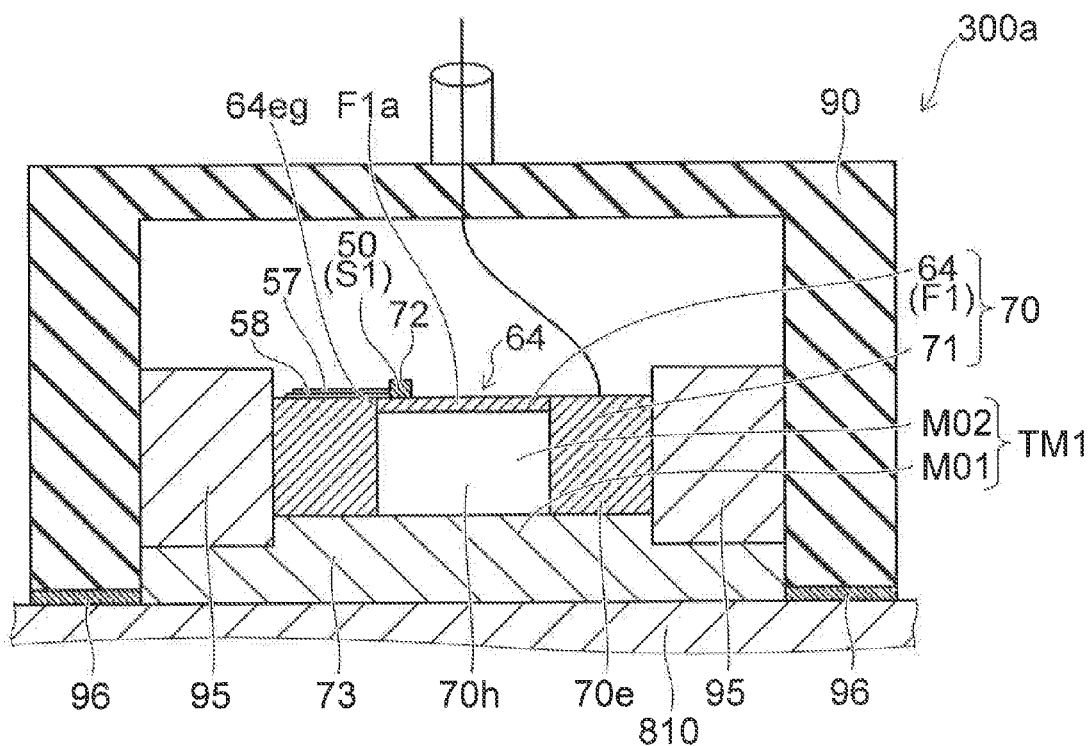
FIG. 1 is a schematic cross-sectional view illustrating an acoustic sensor according to a first embodiment.

According to one embodiment, an acoustic sensor includes a base and a first strain sensing element. The base includes a support and a first film unit supported by the support. The first film unit is flexible. The first strain sensing element is provided on a first surface of the first film unit. The first strain sensing element includes a first magnetic layer, a second magnetic layer, and a first intermediate layer provided between the first magnetic layer and the second magnetic layer. An acoustic wave is transmitted to a first film unit via a first transmitting material provided in contact with the first film unit. An angle between a magnetization of the first magnetic layer and a magnetization of the second magnetic layer is variable in accordance with the acoustic wave.

According to one embodiment, an acoustic sensor includes a base, a first strain sensing element and a first transmitting material. The base includes a support and a first film unit supported by the support. The first film unit is flexible. The first strain sensing element is provided on a first surface of the first film unit. The first strain sensing element includes a first magnetic layer, a second magnetic layer, and a first intermediate layer provided between the first magnetic layer and the second magnetic layer. The first transmitting material is in contact with the first film unit and configured to transmit an acoustic wave to the first film unit.

Various embodiments will be described hereinafter with reference to the accompanying drawings.

The drawings are schematic or conceptual; and the relationships between the thickness and width of portions, the proportions of sizes among portions, etc. are not necessarily the same as the actual values thereof. Further, the dimensions and proportions may be illustrated differently among drawings, even for identical portions.

In the specification of this application and the drawings, components similar to those described in regard to a drawing thereinabove are marked with the same reference numerals, and a detailed description is omitted as appropriate.

First Embodiment

FIG. 1 is a schematic cross-sectional view illustrating an acoustic sensor according to a first embodiment.

As shown in FIG. 1, an acoustic sensor 300a according to the embodiment includes a base 70 and a sensor unit 72. The sensor unit 72 is provided on the base 70, for example. The sensor unit 72 includes a strain sensing element 50 (a first strain sensing element S1). The base 70 includes a support 71 and a transducer thin film 64 (a first film unit F1). The transducer thin film 64 has a film surface 64a. The transducer thin film 64 is flexible. The transducer thin film 64 is deformable. The strain sensing element 50 is fixed to the film surface 64a, for example. The strain sensing element 50 is provided on the film surface 64a, for example.

In the specification, "fixed" is not limited to the strain sensing element and the film surface being directly fixed together, and includes the case where the strain sensing element and the film surface are indirectly fixed via another component. That is, "fixed" refers to the relative positional relationship between the strain sensing element and the film surface being fixed.

The transducer thin film 64 is deformed by a pressure applied from the outside (for example, bends). The transducer thin film 64 transduces strain to the strain sensing element 50. The pressure from the outside includes pressure caused by sound waves, ultrasonic waves, or the like.

The thin film that forms the transducer thin film 64 may be continuously formed on the outside of the portion that is deformed by an external pressure. In the specification, the portion that is deformed by an external pressure is referred to as the transducer thin film. The transducer thin film 64 is surrounded by a fixed end (for example, the edge 64eg). In this example, the support 71 includes the fixed end. The thickness of the transducer thin film 64 is a uniform thickness smaller than the thickness of the fixed end, for example.

The strain sensing element 50 is provided on at least one of the upper surface and the lower surface of the transducer thin film 64, for example. The strain sensing element 50 includes a first magnetic layer 10, a second magnetic layer 20, and a first intermediate layer 15. The first intermediate layer 15 is provided between the first magnetic layer 10 and the second magnetic layer 20.

The strain sensing element 50 is provided on a position of the transducer thin film 64 where the amount of strain is large, for example. That is, the strain sensing element 50 is provided on at least one of a central portion and an edge portion of the transducer thin film 64, for example.

The acoustic sensor 300a according to the embodiment is an acoustic sensor using a spin element. A plurality of strain sensing elements 50 may be provided, for example. The sensitivity is improved by using a plurality of strain sensing elements 50.

In the embodiment, a second strain sensing element may be further provided, for example. The second strain sensing element is provided on a first surface F1a. The second strain sensing element includes a third magnetic layer, a fourth magnetic layer, and a second intermediate layer provided between the third magnetic layer and the fourth magnetic layer (see FIG. 6B). In the embodiment, a plurality of strain sensing elements may be provided, for example. The number of strain sensing elements may be two or more.

The base 70 includes a hollow portion 70h. The base 70 includes a non-hollow portion 70e. The non-hollow portion 70e is juxtaposed to the hollow portion 70h.

The hollow portion 70h is a portion where the material forming the non-hollow portion 70e is not provided. The hollow portion 70h may be filled with a transmitting material (a first transmitting material TM1), for example. The transmitting material contains at least one of a liquid and a solid. The acoustic sensor is used at 0° C. to 80° C., for example. The transmitting material may be in a liquid state at room temperature (for example, 25° C.), for example. The transmitting material may be in a solid state at room temperature, for example. The transmitting material may be in a gel form at room temperature, for example.

The acoustic sensor according to the embodiment (the acoustic sensor 300a) includes the base 70 and the first strain sensing element S1 (the strain sensing element 50). The base 70 includes the support 71 and the first film unit F1 (the transducer thin film 64). The first film unit F1 is supported by the support 71. The first film unit F1 is deformable. The base 70 can house the first transmitting material TM1 in the space partitioned by the support 71 and the first film unit F1 (the hollow portion 70h), for example. The first strain sensing element S1 is provided on the surface of the first film unit F1 (the first surface F1a). The first strain sensing element S1 includes the first magnetic layer 10, the second magnetic layer 20, and the first intermediate layer 15. The first intermediate layer 15 is provided between the first magnetic layer 10 and the second magnetic layer 20.

An acoustic wave is transmitted to the first film unit F1 by the first transmitting material TM1 in contact with the first film unit F1. As described later, the angle between the magnetization of the first magnetic layer 10 and the magnetization of the second magnetic layer 20 can be changed by the acoustic wave received by the first film unit F1.

The acoustic sensor 300a is installed facing a measuring object 810, for example. The first transmitting material TM1 is disposed between the acoustic sensor 300a and the measuring object 810. The acoustic impedance of the first transmitting material TM1 is lower than the acoustic impedance of the measuring object 810.

The hollow portion 70h is filled with a liquid, for example. The acoustic impedance of the liquid put in is lower (smaller) than the acoustic impedance of the measuring object 810, for example. A deformable material may be included in the hollow portion 70h, for example. Thereby, the transducer thin film 64 can be deformed. The acoustic impedance of the deformable material is lower than the acoustic impedance of the measuring object 810, for example.

The acoustic sensor 300a includes the base 70, the first strain sensing element S1, and the first transmitting material TM1. The first transmitting material TM1 is in contact with the first film unit F1. The first transmitting material TM1 is provided between the measuring object 810 and the first film unit F1. The first transmitting material TM1 transmits an acoustic wave to the first film unit F1. The acoustic sensor 300a is an ultrasonic sensor, for example.

The measuring object 810 is a metal, an alloy, a bedrock, concrete, wood, a plant, or others, for example. The acoustic impedance of iron is 46 MRayl at 25° C., for example. The acoustic impedance of copper is 44 MRayl. The acoustic impedance of aluminum is 17 MRayl. The acoustic impedance of concrete is 8 MRayl. The acoustic impedance of wood (evergreen oak) is 3 MRayl.

The medium put in the hollow portion 70h is an alcohol (glycerin), oil, water, mercury, rubber, wax, or others, for example. The acoustic impedances of these are lower than the acoustic impedance of the measuring object 810.

An acoustic coupler 73 and the medium put in the hollow portion 70h constitute an acoustic matching layer, for example. As the acoustic matching layer, glycerin, water, mercury, rubber (for example, styrene-butadiene rubber), or silicone is used, for example. The acoustic impedance of glycerin is 2.4 MRayl at 25° C., for example. The acoustic impedance of water is 1.5 MRayl. The acoustic impedance of mercury is 19.8 MRayl. The acoustic impedance of rubber (for example, styrene-butadiene rubber) is 1.7 MRayl. The acoustic impedance of silicone is 19.6 MRayl.

The acoustic impedance of air is 410 Rayl, for example. The acoustic impedance of air is approximately 1/10,000 of the acoustic impedance of the medium put in the hollow portion 70h and the like (for example, not less than 1/50,000 and not more than 1/1000). If there is gas between the measuring object 810 and the transducer thin film 64, an elastic wave may be reflected at the boundary surface. In this case, it may be difficult to detect the elastic wave using the acoustic sensor.

In this example, the base 70 is fixed to a housing 90 by a base support 95.

The acoustic coupler 73 is put in between the housing 90 and the base 70. The acoustic impedance of the acoustic coupler 73 is lower than the acoustic impedance of the measuring object 810, for example. The material used for the acoustic coupler 73 may not be the same as the material put in the hollow portion 70h. That is, the acoustic matching layer may be a multiple-layer structure.

When the material of the acoustic coupler 73 and the material of the medium put in the hollow portion 70h are different from each other, the acoustic matching layer is a multiple-layer structure, for example. Also when an acoustic coupler 73 of a multiple-layer structure is used, the acoustic matching layer is a multiple-layer structure. When an acoustic matching layer of a multiple-layer structure is used, it is preferable that the acoustic impedances of the layers be set to decrease gradually from the measuring object 810 toward the transducer thin film 64, for example. Thereby, the energy loss in the propagation path of the elastic wave is suppressed.

The filler (the first transmitting material TM1) includes a first layer M01 and a second layer M02 provided between the first layer M01 and the first film unit F1, for example. The acoustic impedance of the second layer M02 is preferably lower than the acoustic impedance of the first layer M01. The acoustic impedance of the second layer M02 may be higher than the acoustic impedance of the first layer M01, for example.

When a pressure (including a sound, an ultrasonic wave, or the like) is applied to the transducer thin film 64 from the outside, the transducer thin film 64 is deformed. Accordingly, a strain is generated in the strain sensor (the sensor unit 72) provided on the transducer thin film 64. Thus, the transducer thin film 64 transmits (transduces) a signal of pressure to the sensor unit 72. The signal of pressure is converted to a signal of strain in the sensor unit 72.

The strain sensor (the sensor unit 72) is provided on at least one of the upper surface and the lower surface of the transducer thin film 64.

In this example, the transducer thin film 64 is provided on the upper side of the hollow portion 70h.

A surface parallel to the film surface 64a is defined as the X-Y plane. In the case where the film surface 64a is not a flat surface, a plane including the edge 64eg of the film surface 64a is defined as the X-Y plane. The direction perpendicular to the X-Y plane is defined as the Z-axis direction.

The acoustic sensor 300a is susceptible to external noise. In this example, components such as the base 70 and the sensor unit 72 mentioned above are surrounded by the housing 90.

For the housing 90, aluminum, stainless steel, or the like is used, for example. Thereby, the housing 90 functions as a magnetic shield, for example.

The acoustic sensor is fixed to the measuring object 810, for example. The housing 90 is fixed to the measuring object 810 by a fixing unit 96 (a fixing material).

For the fixing unit 96, an epoxy-based adhesive, wax, and the like are used, for example. The acoustic sensor 300a is stuck to the measuring object 810 so that there is no gas between the measuring object 810 and the acoustic coupler 73.

The housing 90 is provided in the acoustic sensor 300a, for example. The base 70, the first strain sensing element S1, and the first transmitting material TM1 are provided in the housing 90.

Figure 2:
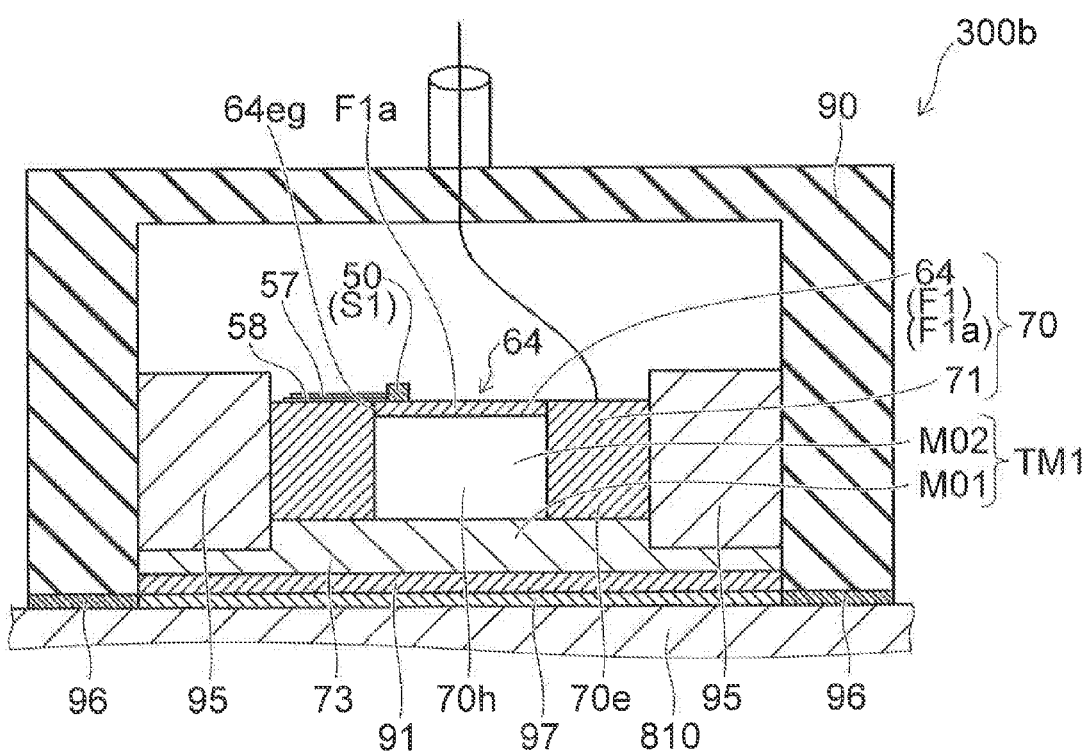
FIG. 2 is a schematic cross-sectional view illustrating an acoustic sensor according to the first embodiment.

FIG. 2 is a schematic cross-sectional view illustrating an acoustic sensor according to the first embodiment.

As shown in FIG. 2, a bottom plate 91 integrated with the housing 90 may be provided on the bottom surface of an acoustic sensor 300b. The first transmitting material is disposed between the bottom plate 91 and the first film unit F1. In this example, an acoustic coupler material 97 is provided between the bottom plate 91 and the measuring object 810. The acoustic sensor 300b is stuck to the measuring object 810.

As the acoustic coupler material 97, an epoxy-based adhesive, wax, grease, a silicone compound, or the like is used, for example. The acoustic sensor 300b is stuck to the measuring object 810 so that there is no gas between the measuring object 810 and the acoustic coupler material 97.

When the measuring object 810 is a metal or the like, a magnet or the like may be used as the fixing unit 96, for example.

The transducer thin film 64 includes an insulating layer, for example. The transducer thin film 64 contains a metal material, for example. The transducer thin film 64 contains silicon oxide, silicon nitride, or the like, for example. The thickness of the transducer thin film 64 is not less than 200 nm and not more than 3 μm, for example. It is preferably not less than 300 nm and not more than 1.5 μm. The diameter of the transducer thin film 64 is not less than 1 μm and not more than 3 mm, for example. It is preferably not less than 60 μm and not more than 1 mm. The transducer thin film 64 is flexible in the Z-axis direction perpendicular to the film surface 64a, for example.

One end of the strain sensing element 50 is connected to a first interconnection 57. The other end of the strain sensing element 50 is connected to a second interconnection 58. The first interconnection 57 and the second interconnection 58 extend from the strain sensing element 50 toward the base 70, for example.

When the acoustic matching layer includes a multiple-layer structure, first, the hollow portion 70h of the base 70 is filled with a liquid (the first stage), for example. After that, another liquid (the second stage) is enclosed in a flat manner on the lower side of the base 70 in the housing 90. Next, grease or an adhesive is applied to the contact surface between the measuring object 810 and the acoustic sensor, for example.

A magnetic shield package is used as the housing 90, for example. A metal shield film is formed above a chip, and the housing 90 forms a metal plate shield. A metal shield film is formed above a chip, for example.

Figure 3:
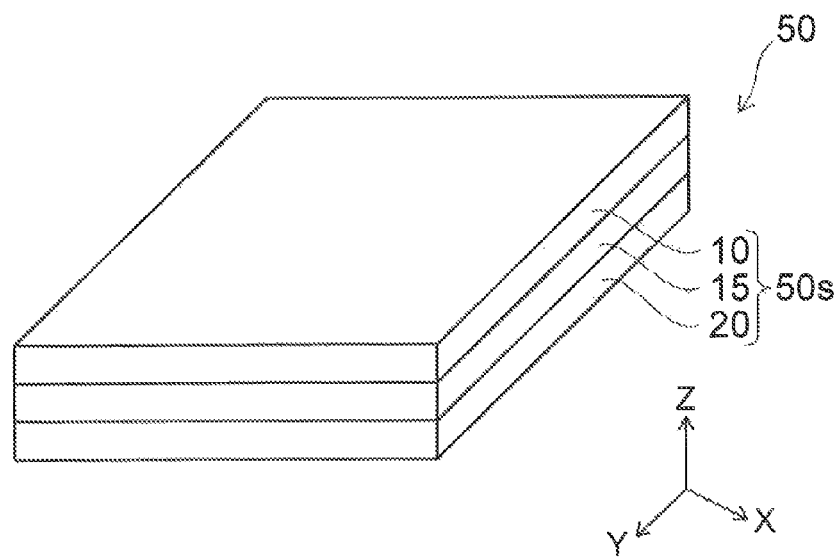
FIG. 3 is a schematic perspective view illustrating part of the acoustic sensor according to the embodiment.

FIG. 3 is a schematic perspective view illustrating part of the acoustic sensor according to the embodiment.

As shown in FIG. 3, a strain resistance change unit 50s (the strain sensing element 50) includes the first magnetic layer 10, the second magnetic layer 20, and the first intermediate layer 15 provided between the first magnetic layer 10 and the second magnetic layer 20, for example. The first intermediate layer 15 is a nonmagnetic layer.

In this example, the first magnetic layer 10 is a magnetization free layer. The second magnetic layer 20 is a magnetization fixed layer or a magnetization free layer, for example.

The direction from the second magnetic layer 20 toward the first magnetic layer 10 is defined as the Z-axis direction. One direction perpendicular to the Z-axis direction is defined as the X-axis direction. The direction perpendicular to the X-axis direction and the Z-axis direction is defined as the Y-axis direction.

In the following, operations of the strain sensing element 50 are described for the case where the second magnetic layer 20 is a magnetization fixed layer and the first magnetic layer 10 is a magnetization free layer. In the strain sensing element 50, "inverse magnetostriction effect" that ferromagnetic materials have and "MR effect" that is exhibited in the strain resistance change unit 50s are utilized.

The "MR effect" is a phenomenon in which, in a stacked film including a magnetic material, the value of the electric resistance of the stacked film changes due to the change in magnetization of the magnetic material caused by the application of an external magnetic field. The MR effect includes GMR (giant magnetoresistance) effect, TMR (tunneling magnetoresistance) effect, or the like, for example. The MR effect is exhibited by passing a current through the strain resistance change unit 50s to read the change in relative angle between the magnetization directions as an electric resistance change. Based on the stress applied to the strain sensing element 50, a tensile stress is applied to the strain resistance change unit 50s, for example. The MR effect is exhibited due to the inverse magnetostriction effect when the direction of the magnetization of the first magnetic layer 10 (a magnetization free layer) and the direction of the tensile stress applied to the second magnetic layer 20 are different. The resistance in the low resistance state is denoted by R, and the amount of change in electric resistance that changes due to the MR effect is denoted by ΔR. ΔR/R is referred to as the "MR ratio."

Figure 4A:
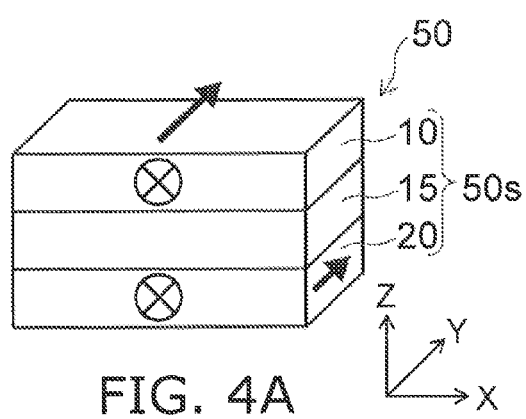
FIG. 4A to FIG. 4C are schematic perspective views illustrating operations of the acoustic sensor according to the embodiment.
Figure 4B:
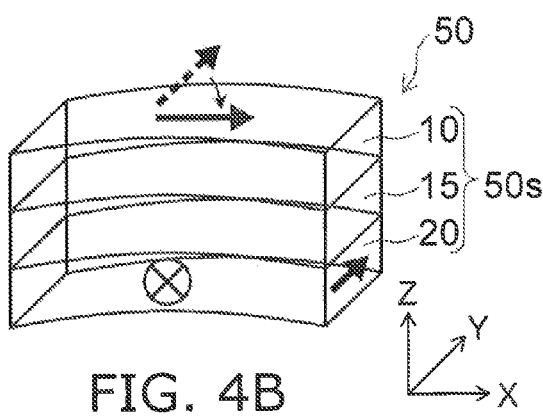
Figure 4C:
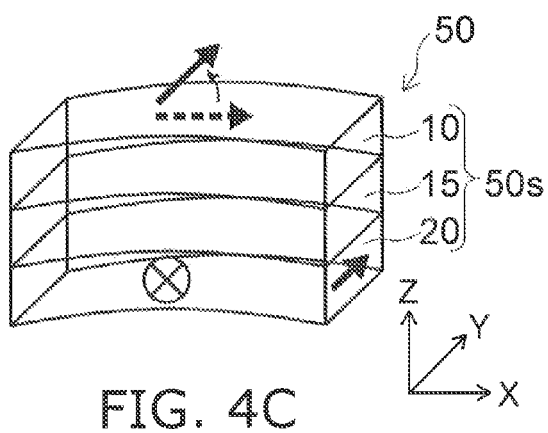

FIG. 4A to FIG. 4C are schematic perspective views illustrating operations of the acoustic sensor according to the embodiment.

The drawings illustrate relationships between the magnetization direction in the strain sensing element 50 and the direction of tensile stress.

FIG. 4A shows a state where no tensile stress is applied. In this example, the direction of the magnetization of the second magnetic layer 20 (a magnetization fixed layer) is the same as the direction of the magnetization of the first magnetic layer 10 (a magnetization free layer).

FIG. 4B shows a state where a tensile stress is applied. In this example, a tensile stress is applied along the X-axis direction. The tensile stress along the X-axis direction is applied to the strain sensing element 50 by the deformation of the transducer thin film 64, for example. In this example, the tensile stress is applied in a direction orthogonal to the direction of the magnetization of the second magnetic layer 20 (a magnetization fixed layer) and the direction of the magnetization of the first magnetic layer 10 (a magnetization free layer) (in this example, the Y-axis direction). At this time, the magnetization of the first magnetic layer 10 (a magnetization free layer) rotates so as to become the same direction as the direction of the tensile stress. This is referred to as "inverse magnetostriction effect." The magnetization of the second magnetic layer 20 (a magnetization fixed layer) is fixed. Thus, by the rotation of the magnetization of the first magnetic layer 10 (a magnetization free layer), the relative angle between the direction of the magnetization of the second magnetic layer 20 (a magnetization fixed layer) and the direction of the magnetization of the first magnetic layer 10 (a magnetization free layer) is changed.

The magnetization direction of the second magnetic layer 20 (a magnetization fixed layer) illustrated in FIG. 4B is an example. The magnetization direction may not be the direction shown in the drawing.

The easy axis of magnetization in the inverse magnetostriction effect varies with the sign of the magnetostriction constant of the ferromagnetic material.

A large number of materials exhibiting a large inverse magnetostriction effect have a positive magnetostriction constant. In the case where the sign of the magnetostriction constant is plus, the direction of the magnetization easy axis is the direction of the tensile stress, as described above. At this time, the magnetization of the first magnetic layer 10 (a magnetization free layer) rotates toward the direction of the magnetization easy axis, as mentioned above.

In the case where the magnetostriction constant of the first magnetic layer 10 (a magnetization free layer) is positive, the magnetization direction of the first magnetic layer 10 (a magnetization free layer) is set to a direction different from the direction of the tensile stress, for example. On the other hand, in the case where the magnetostriction constant is negative, a direction perpendicular to the direction of the tensile stress is the direction of the magnetization easy axis.

FIG. 4C shows a state where the magnetostriction constant of the first magnetic layer 10 is negative. In this case, the magnetization direction of the first magnetic layer 10 (a magnetization free layer) is set to a direction different from the directions perpendicular to the direction (in this example, the X-axis direction) of the tensile stress.

In this example, the magnetization direction of the first magnetic layer 10 is shown as the magnetization direction of the second magnetic layer 20 (a magnetization fixed layer). The magnetization direction may not be the direction shown in the drawing.

The electric resistance of the strain sensing element 50 (the strain resistance change unit 50s) changes due to the MR effect in accordance with the angle between the magnetization direction of the first magnetic layer 10 and the magnetization direction of the second magnetic layer 20, for example.

The magnetostriction constant ($\lambda s$) represents the magnitude of the deformation when a ferromagnetic layer is saturated in a certain direction by an external magnetic field. It is assumed that the length of a magnetic layer is L in a state where there is no external magnetic field, for example. It is assumed that the length of the magnetic layer has changed by ΔL when an external magnetic field is applied. At this time, the magnetostriction constant $\lambda s$ is expressed by ΔL/L. The amount of change varies with the magnitude of the magnetic field. The magnetostriction constant $\lambda s$ is ΔL/L in a state where the magnetization of the magnetic layer is saturated by a sufficient magnetic field.

In the case where the second magnetic layer 20 is a magnetization fixed layer, an alloy material containing at least one of Fe, Co, and Ni is used for the second magnetic layer 20, for example. Furthermore, a material in which an additive element is added to the material mentioned above or the like is used for the second magnetic layer 20. CoFe alloy, CoFeB alloy, NiFe alloy, or the like is used for the second magnetic layer 20, for example. The thickness of the second magnetic layer 20 is not less than 2 nanometers (nm) and not more than 6 nanometers (nm), for example.

For the first intermediate layer 15, a metal or an insulator is used, for example. For the first intermediate layer 15, a metal containing at least one of Cu, Au, and Ag and the like are used, for example. In the case where a metal is used as the first intermediate layer 15, the thickness of the first intermediate layer 15 is not less than 1 nm and not more than 7 nm, for example. For the first intermediate layer 15, an insulator containing at least one of Mg, Al, Ti, and Zn and oxygen is used, for example. A magnesium oxide (MgO etc.), an aluminum oxide ($Al_2O_3$ etc.), a titanium oxide (TiO etc.), a zing oxide (ZnO etc.), or the like is used as the first intermediate layer 15, for example. In the case where an insulator is used as the first intermediate layer 15, the thickness of the first intermediate layer 15 is not less than 1 nm and not more than 3 nm, for example.

In the case where the first magnetic layer 10 is a magnetization free layer, an alloy material containing at least one of Fe, Co, and Ni is used for the first magnetic layer 10, for example. A material in which an additive element is added to the material mentioned above is used, for example.

For the first magnetic layer 10, a material with a large magnetostriction is used. Specifically, a material of which the absolute value of the magnetostriction is larger than $10^{-5}$ is used. Thereby, the magnetization changes sensitively with the strain. For the first magnetic layer 10, either a material having a positive magnetostriction or a material having a negative magnetostriction may be used.

For the first magnetic layer 10, FeCo alloy, NiFe alloy, or the like may be used, for example. For the first magnetic layer 10, Fe—Co—Si—B alloy may be used, for example. For the first magnetic layer 10, a Tb-M-Fe alloy, a Tb-M1-Fe-M2 alloy, an Fe-M3-M4-B alloy, or the like may be used. M represents Sm, Eu, Gd, Dy, Ho, or Er. M1 represents Sm, Eu, Gd, Dy, Ho, or Er. M2 represents Ti, Cr, Mn, Co, Cu, Nb, Mo, W, or Ta. M3 represents Ti, Cr, Mn, Co, Cu, Nb, Mo, W, or Ta. M4 represents Ce, Pr, Nd, Sm, Tb, Dy, or Er. A ferrite is $Fe_3O_4$, $(FeCo)_3O_4$, or the like. In the Tb-M-Fe alloy, the Tb-M1-Fe-M2 alloy, the Fe-M3-M4-B alloy, or the like, the λs is larger than 100 ppm, for example. For the first magnetic layer 10, Ni, Al—Fe, a ferrite, or the like may be used, for example.

The thickness of the first magnetic layer 10 is 2 nm or more, for example.

The first magnetic layer 10 includes a two-layer structure, for example. As the first magnetic layer 10, a stacked structure including an FeCo alloy layer is used, for example. For the layer stacked with the layer of FeCo alloy, Fe—Co—Si—B alloy is used, for example. For the layer stacked with the layer of FeCo alloy, a Tb-M-Fe alloy, a Tb-M1-Fe-M2 alloy, or an Fe-M3-M4-B alloy is used, for example. M represents Sm, Eu, Gd, Dy, Ho, or Er. M1 represents Sm, Eu, Gd, Dy, Ho, or Er. M2 represents Ti, Cr, Mn, Co, Cu, Nb, Mo, W, or Ta. M3 represents Ti, Cr, Mn, Co, Cu, Nb, Mo, W, or Ta. M4 represents Ce, Pr, Nd, Sm, Tb, Dy, or Er. A ferrite is $Fe_3O_4$, $(FeCo)_3O_4$, or the like. In the Tb-M-Fe alloy, the Tb-M1-Fe-M2 alloy, or the Fe-M3-M4-B alloy, the λs is larger than 100 ppm, for example. For the layer stacked with the layer of FeCo alloy, a layer containing at least one of Ni, Al—Fe, and a ferrite is used, for example.

When the first intermediate layer 15 is a metal, the GMR effect is exhibited, for example. When the first intermediate layer 15 is an insulator, the TMR effect is exhibited. In the strain sensing element 50, the CPP (current perpendicular to plane)-GMR effect in which a current is passed along the stacking direction of the strain resistance change unit 50s is used, for example.

A CCP (current-confined-path) spacer layer may be used as the first intermediate layer 15. The CCP spacer layer includes, in part of an insulating layer, a plurality of metal current paths penetrating in the film thickness direction, for example. The width of the metal current path is 1 nm or more, for example (for example, the diameter is approximately 5 nm). The CPP-GMR effect is used also in this case.

Thus, in the embodiment, the inverse magnetostriction phenomenon in the strain sensing element 50 is used. Thereby, high-sensitivity sensing becomes possible. When the inverse magnetostriction effect is used, the magnetization direction of at least one of the first magnetic layer 10 and the second magnetic layer 20 changes with the strain applied from the outside, for example. The relative angle between the magnetizations of the two magnetic layers changes with the strain applied from the outside (the presence or absence, the level thereof, etc.). Since the electric resistance changes with the strain applied from the outside, the strain sensing element 50 functions as a pressure sensor.

Figure 5A:
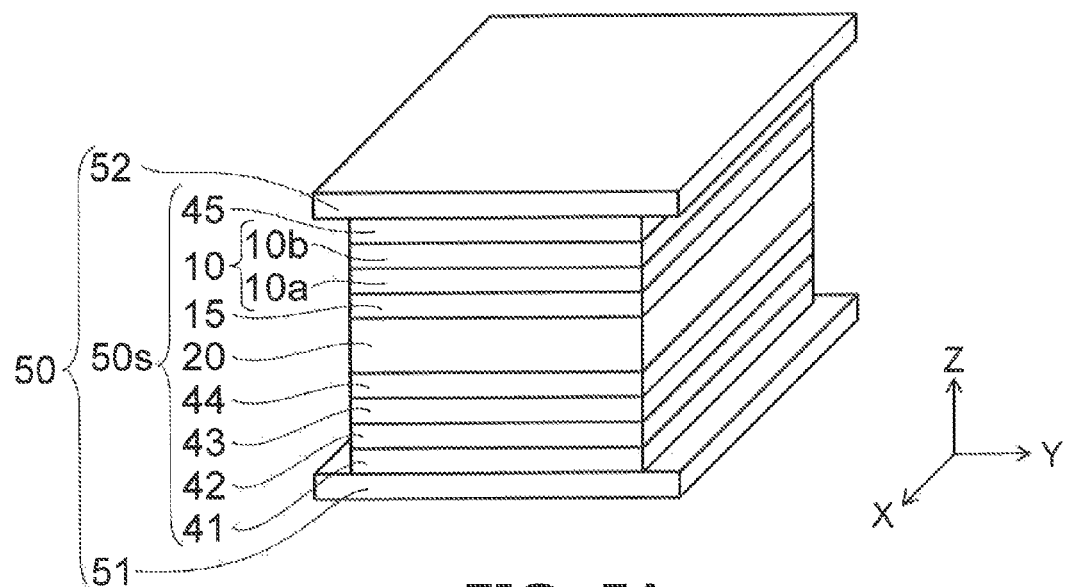
FIG. 5A and FIG. 5B are schematic perspective views illustrating the acoustic sensor according to the embodiment.
Figure 5B:
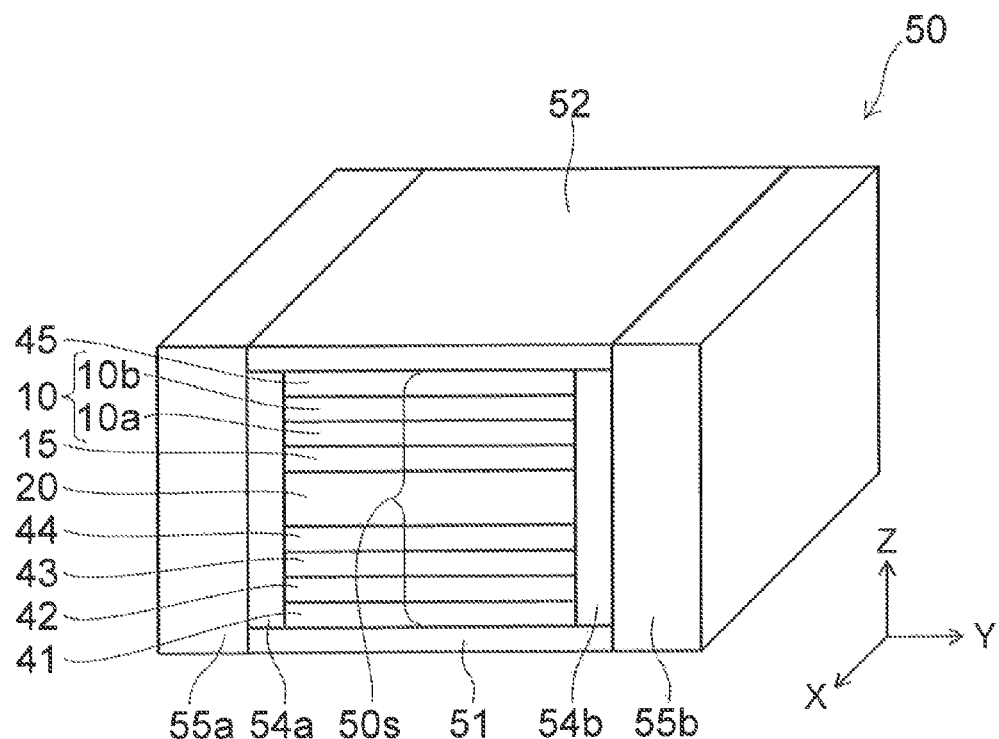

FIG. 5A and FIG. 5B are schematic perspective views illustrating the acoustic sensor according to the embodiment.

As shown in FIG. 5A, the strain sensing element 50 includes a first electrode 51 and a second electrode 52, for example. The strain resistance change unit 50s is provided between the first electrode 51 and the second electrode 52. In this example, in the strain resistance change unit 50s, a buffer layer 41, an antiferromagnetic layer 42, a magnetic layer 43, a Ru layer 44, the second magnetic layer 20, the first intermediate layer 15, the first magnetic layer 10, and a cap layer 45 are provided in this order from the first electrode 51 side toward the second electrode 52 side. The thickness of the buffer layer 41 is not less than 1 nm and not more than 10 nm, for example. The buffer layer 41 is an amorphous layer containing Ta or Ti, for example. The buffer layer 41 may serve also as a seed layer. As the buffer layer 41, a layer of Ru, NiFe, or the like is used, for example. The layer of Ru, NiFe, or the like serves as a seed layer for the promotion of crystal orientation. A stacked film of these may be used as the buffer layer 41.

The thickness of the antiferromagnetic layer 42 is not less than 5 nm and not more than 10 nm, for example. The thickness of the magnetic layer 43 is not less than 2 nm and not more than 6 nm, for example. The thickness of the second magnetic layer 20 is not less than 2 nm and not more than 5 nm, for example. The thickness of the first intermediate layer 15 is not less than 1 nm and not more than 3 nm, for example. The thickness of the first magnetic layer is not less than 2 nm and not more than 5 nm, for example. The thickness of the cap layer 45 is not less than 1 nm and not more than 5 nm, for example.

As the second magnetic layer 20, a magnetic stacked film is used, for example. The first magnetic layer 10 includes a magnetic stacked film 10a for increasing the MR ratio and a high magnetostriction magnetic film 10b provided between the magnetic stacked film 10a and the cap layer 45. The thickness of the magnetic stacked film 10a is not less than 1 nm and not more than 3 nm, for example. The magnetic stacked film 10a contains CoFe, for example. The thickness of the high magnetostriction magnetic film is not less than 1 nm and not more than 5 nm, for example.

The first electrode 51 contains at least one of Au, Cu, Ta, and Al, for example. These are nonmagnetic. The second electrode 52 contains at least one of Au, Cu, Ta, and Al, for example. As the first electrode 51 and the second electrode 52, a soft magnetic material may be used; thereby, magnetic noise from the outside that influences the strain resistance change unit 50s is reduced. As the soft magnetic material, permalloy (NiFe alloy) and silicon steel (FeSi alloy) are used, for example. The strain sensing element 50 is covered with an insulator such as an aluminum oxide (for example, $Al_2O_3$) and a silicon oxide (for example, $SiO_2$), for example. Thereby, leakage current to the surroundings is suppressed.

The magnetization direction of at least one of the first magnetic layer 10 and the second magnetic layer 20 changes in accordance with the stress. The absolute value of the magnetostriction constant of at least one magnetic layer (the magnetic layer of which the magnetization direction changes in accordance with the stress) is set to $10^{-5}$ or more, for example. Thereby, the magnetization direction changes in accordance with the strain applied from the outside, due to the inverse magnetostriction effect. For at least one of the first magnetic layer 10 and the second magnetic layer 20, an alloy containing at least one of Fe, Co, and Ni or the like is used, for example. The magnetostriction constant is set large by the element used, additive elements, etc. The absolute value of the magnetostriction constant is preferably large. The absolute values of the magnetostriction constants of materials that can be used as practical devices are approximately $10^{-2}$ or less, for example.

As the first intermediate layer 15, an oxide such as MgO is used, for example. The magnetostriction constant of a magnetic layer on a MgO layer is plus, for example. In the case where the first magnetic layer 10 is formed on the first intermediate layer 15, a magnetization free layer with a stacked configuration of CoFeB/CoFe/NiFe is used as the first magnetic layer 10, for example. When the uppermost NiFe layer is made Ni-rich, the magnetostriction constant of the NiFe layer is negative and the absolute value thereof is large. The uppermost NiFe layer is not Ni-rich as compared to the permalloy of $Ni_{81}Fe_{19}$, for example. Thereby, the cancellation of the plus magnetostriction on an oxide layer is suppressed, for example. The ratio of Ni in the uppermost NiFe layer is preferably set less than 80 atomic percent (atomic %). In the case where a magnetization free layer is used as the first magnetic layer 10, the thickness of the first magnetic layer 10 is preferably not less than 1 nm and not more than 20 nm, for example.

In the case where the first magnetic layer 10 is a magnetization free layer, the second magnetic layer 20 may be either a magnetization fixed layer or a magnetization free layer. In the case where the second magnetic layer 20 is a magnetization fixed layer, substantially the magnetization direction of the second magnetic layer 20 does not change even when a strain is applied from the outside. The electric resistance changes with the relative angle between the magnetizations of the first magnetic layer 10 and the second magnetic layer 20. The strain is sensed by the change in electric resistance.

In the case where both the first magnetic layer 10 and the second magnetic layer 20 are a magnetization free layer, the magnetostriction constant of the first magnetic layer 10 is set different from the magnetostriction constant of the second magnetic layer 20, for example.

In the case where the second magnetic layer 20 is either a magnetization fixed layer or a magnetization free layer, the thickness of the second magnetic layer 20 is preferably not less than 1 nm and not more than 20 nm, for example.

In the case where the second magnetic layer 20 is a magnetization fixed layer, a synthetic AF structure including a stacked structure of an antimagnetic layer/a magnetic layer/a Ru layer/a magnetic layer and the like may be used as the second magnetic layer 20, for example. For the antimagnetic layer, IrMn and the like are used, for example. A hard bias layer may be provided as described later.

The spin of a magnetic layer is used in the strain sensing element 50. The area of the strain sensing element 50 is a very small size, for example. Assuming that the shape of the strain sensing element 50 is a square, the size of the strain sensing element 50 is 10 nm or more, for example 20 nm or more, in terms of the length of one side, for example.

The area of the strain sensing element 50 is sufficiently smaller than the area of the transducer thin film 64 that is deformed by pressure, for example. Here, the transducer thin film is the portion surrounded by the fixed end, as described above. The transducer thin film is designed so as to be deformed by an external pressure. The thickness of the transducer thin film is a uniform thickness smaller than the thickness of the fixed end. The area of the strain sensing element 50 (The area of the strain sensing element 50 when projected onto the transducer thin film 64) is not more than ⅕ of the area of the transducer thin film 64 in the substrate plane, for example. The diameter of the transducer thin film 64 is approximately not less than 60 μm and not more than 600 μm, for example. When the diameter of the transducer thin film 64 is as small as approximately 60 μm, the length of one side of the strain sensing element 50 is 12 μm or less, for example. When the diameter of the transducer thin film is 600 μm, the length of one side of the strain sensing element 50 is 120 μm or less. This value is the upper limit of the size of the strain sensing element 50, for example.

As compared to the value of this upper limit, the size of the length of one side of not less than 10 nm and not more than 20 nm mentioned above is extremely small. It is not necessary to set the size of the strain sensing element 50 excessively small, for example. Thereby, the processing accuracy of the element is ensured, for example. Thus, the size of one side of the strain sensing element 50 is set approximately not less than 0.5 μm and not more than 20 μm, for example. If the element size is extremely small, the magnitude of the antimagnetic field generated in the strain sensing element 50 is increased; thus, the bias control of the strain sensing element 50 may be difficult. When the element size is large, the handling of the element is easy in the engineering viewpoint. From this point of view, not less than 0.5 μm and not more than 20 μm are preferable sizes, as described above.

The length along the X-axis direction of the strain sensing element 50 is not less than 20 nm and not more than 10 μm, for example. The length along the X-axis direction of the strain sensing element 50 is preferably not less than 200 nm and not more than 5 μm.

The length along the Y-axis direction of the strain sensing element 50 is not less than 20 nm and not more than 10 μm, for example. The length along the Y-axis direction of the strain sensing element 50 is preferably not less than 200 nm and not more than 5 μm.

The length along the Z-axis direction (the direction perpendicular to the X-Y plane) of the strain sensing element 50 is not less than 20 nm and not more than 100 nm, for example.

The length along the X-axis direction of the strain sensing element 50 may be equal to or different from the length along the Y-axis direction of the strain sensing element 50. When the length along the X-axis direction of the strain sensing element 50 and the length along the Y-axis direction of the strain sensing element 50 are different, shape magnetic anisotropy occurs, for example. Thereby, the magnetization direction of the first magnetic layer 10 can be biased to an appropriate position, and the first magnetic layer 10 can be made into a single magnetic domain.

The direction of the current passed through the strain sensing element 50 may be either the direction from the first magnetic layer 10 toward the second magnetic layer 20, or the direction from the second magnetic layer 20 toward the first magnetic layer 10.

As shown in FIG. 5B, the strain sensing element 50 includes bias layers 55a and 55b (hard bias layers), for example. The bias layers 55a and 55b are provided facing the strain resistance change unit 50s, for example.

In this example, the second magnetic layer 20 is a magnetization fixed layer. The bias layer 55a is juxtaposed to the second magnetic layer 20. The bias layer 55b is juxtaposed to the second magnetic layer 20. The strain sensing element 50 includes the strain resistance change unit 50s between the bias layers 55a and 55b. An insulating layer 54a is provided between the bias layer 55a and the strain resistance change unit 50s. An insulating layer 54b is provided between the bias layer 55b and the strain resistance change unit 50s.

The bias layers 55a and 55b apply a bias magnetic field to the first magnetic layer 10, for example. Thereby, the magnetization direction of the first magnetic layer 10 can be biased to an appropriate position, and the first magnetic layer 10 can be made into a single magnetic domain.

The size (in this example, the length along the Y-axis direction) of each of the bias layers 55a and 55b is not less than 100 nm and not more than 10 μm, for example.

The size (in this example, the length along the Y-axis direction) of each of the insulating layers 54a and 54b is not less than 1 nm and not more than 5 nm, for example.

The embodiment can provide a high-sensitivity acoustic sensor. The embodiment can provide an acoustic sensor that can monitor objects with high sensitivity in real time, for example.

The acoustic sensor according to the embodiment can be used as a sensor that detects damage in measuring objects, for example. The acoustic sensor according to the embodiment can be used for systems for detecting faults of measuring objects. Magnetism is utilized in the acoustic sensor according to the embodiment. Thereby, objects can be monitored with high sensitivity.

The acoustic sensor according to the embodiment is used for non-destructive testing, for example. In non-destructive testing, damage such as cracks generated in mechanical parts and fabrics is detected without breaking the objects. The acoustic sensor is widely used in non-destructive testing.

The method of non-destructive testing using an acoustic sensor is roughly categorized into the ultrasonic detection method and the acoustic emission method. In the ultrasonic detection method, an ultrasonic wave is sent and received by an acoustic sensor. In the acoustic emission method, acoustic emission generated by damage of a measuring object is received. The acoustic emission is a phenomenon based on the emission of strain energy stored in the measuring object, for example. The acoustic emission is generated by the deformation of a material or the occurrence of a crack. The strain energy is emitted as an elastic wave.

In the ultrasonic detection method, a measuring object is investigated by a sensor installed in periodic inspection or at the time of abnormality. In the ultrasonic detection method, it is difficult to assess whether safe performance is maintained or not after testing. In the ultrasonic detection method, even if an abnormality has occurred at a time between tests, the occurrence of the abnormality is not revealed until the next test. If testing using the ultrasonic detection method is made on a short cycle, costs are increased. There are restrictions on the use of the measuring object during testing. The ultrasonic detection method may be accompanied by destructive testing.

The acoustic sensor of the embodiment is attached to the measuring object 810 at all times, for example. The measuring object 810 is measured using acoustic emission, for example. Thereby, damage generated in the measuring object 810 is detected with high sensitivity in real time.

In an acoustic emission sensor of a reference example, a piezoelectric material such as PZT (lead zirconate titanate) is used for the sensor unit, for example. In the acoustic emission sensor, the vicinity of the resonance point is actively used. Thereby, a small signal can be detected, for example.

The frequency of the acoustic emission wave varies with the material of the measuring object. In the case of metals, the frequency of the acoustic emission wave is approximately not less than 100 kHz and not more than 1 MHz. In the case of bedrocks, the frequency of the acoustic emission wave is approximately not less than 10 kHz and not more than 100 kHz, for example.

Piezoelectric materials typified by PZT have not only vertical piezoelectric effect in which, when an electric field is applied in the polarization direction, the material expands and contracts in this direction, but also horizontal piezoelectric effect in which the material contracts in the direction orthogonal to the electric field direction when it expands in the electric field direction, and the material expands in the direction orthogonal to the electric field direction when it contracts in the electric field direction. The acoustic emission sensor of the reference example mainly utilizes the vertical piezoelectric effect. In this case, the resonance frequency is mainly determined by the thickness of the piezoelectric material, and the resonance frequency is inversely proportional to the thickness of the piezoelectric material. In piezoelectric materials with a relatively low resonance frequency, such as not less than 10 kHz and less than 100 kHz, the thickness of the piezoelectric material is large. To obtain a small-sized high-sensitivity shape, the ratio between thickness (height) and width (diameter) is almost one. In this case, a composite deformation in which a strain in the width direction is combined with a strain in the thickness direction occurs. That is, a pure oscillation mode cannot be obtained.

On the other hand, in a sensor of a reference example using MEMS (micro-electro-mechanical systems) technology not using magnetism, the sensitivity is low in the ultrasonic range. Thus, the MEMS sensor not using magnetism is used mostly in the sonic range.

In contrast, magnetism is used in the acoustic sensor according to the embodiment. By the embodiment, high sensitivity is obtained even on the high frequency side as compared to the MEMS sensor of the reference example not using magnetism. Thereby, a high-sensitivity acoustic sensor can be provided. The resonance frequency in the sensor unit 72 is 100 kHz or more, for example. The resonance frequency in the sensor unit 72 may be 200 kHz or more, for example. The resonance frequency in the sensor unit 72 is 2 MHz or less, for example.

Second Embodiment

FIG. 6A to FIG. 6D are schematic views illustrating acoustic sensors according to a second embodiment.

Figure 6A:
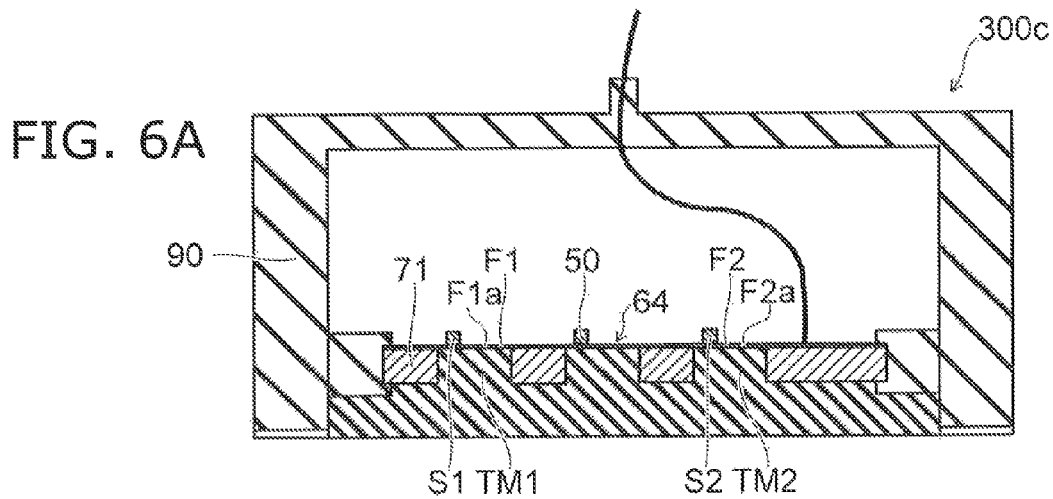
FIG. 6A to FIG. 6D are schematic views illustrating acoustic sensors according to a second embodiment.
Figure 6B:
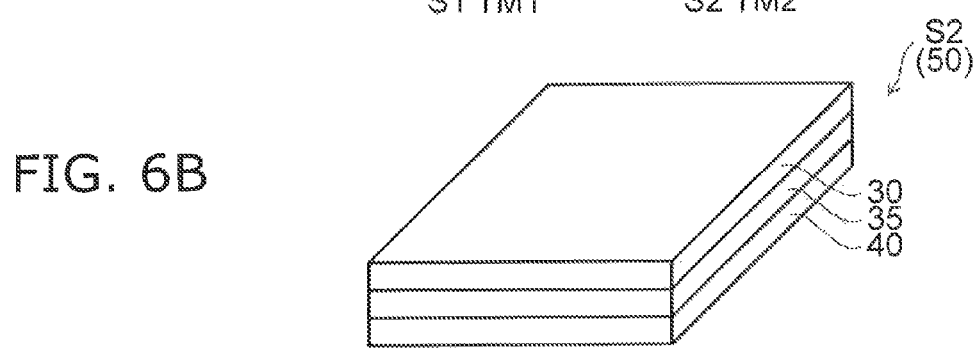

FIG. 6A is a schematic cross-sectional view of an acoustic sensor. FIG. 6B is a schematic perspective view of part of the acoustic sensor.

In an acoustic sensor 300c illustrated in FIG. 6A, a plurality of sensor units 72 are provided. The sizes of the plurality of transducer thin films and the sizes of the plurality of strain sensing elements may be the same or different.

The acoustic sensor 300c further includes a second strain sensing element S2 and a second transmitting material TM2, in addition to the first strain sensing element S1, the first film unit F1, and the first transmitting material TM1. The base 70 further includes a second film unit F2. The second film unit F2 is supported by the support 71. The second strain sensing element S2 is provided on the surface of the second film unit F2 (a second surface F2a).

The second transmitting material TM2 is in contact with the second film unit F2. The second transmitting material TM2 transmits an acoustic wave to the second film unit F2. The second transmitting material TM2 is disposed in the space partitioned by the support 71 and the second film unit F2, for example.

FIG. 6B shows the second strain sensing element S2. The second strain sensing element S2 includes a third magnetic layer 30, a fourth magnetic layer 40, and a second intermediate layer 35. The second intermediate layer 35 is provided between the third magnetic layer 30 and the fourth magnetic layer 40. The configuration and material described in regard to the first strain sensing element S1 may be used for the configuration, material, etc. of each layer included in the second strain sensing element S2, for example.

Figure 6C:
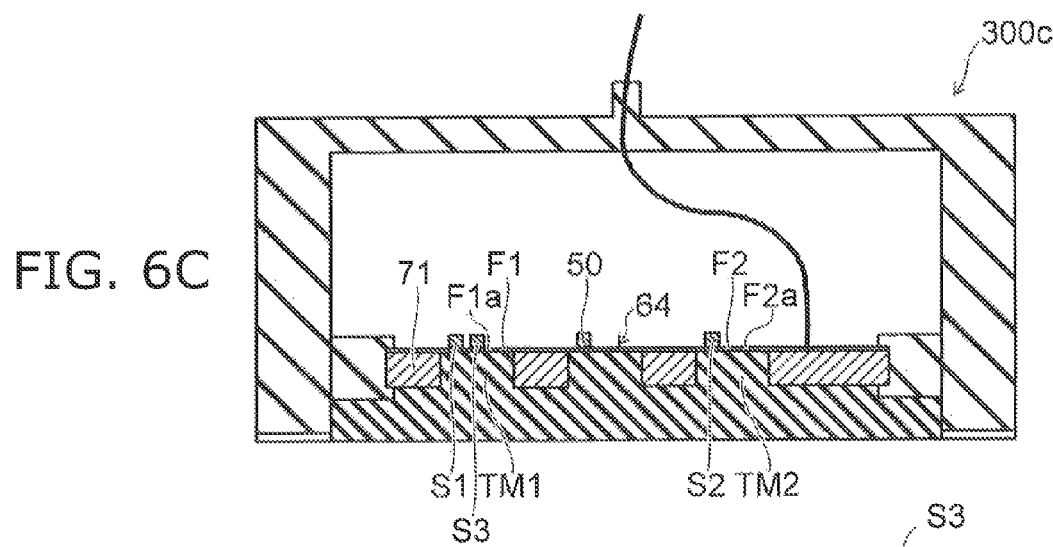
Figure 6D:
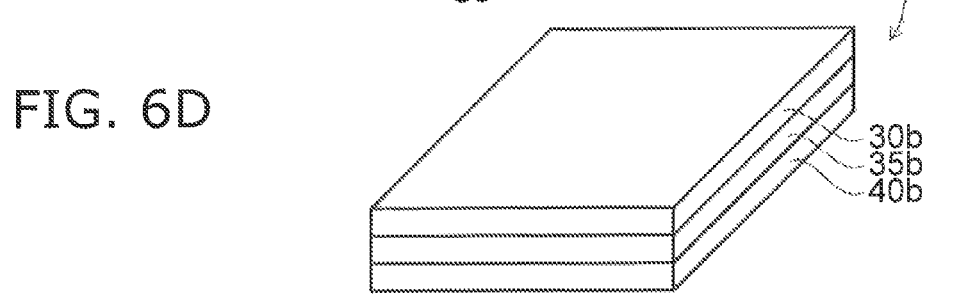

FIG. 6C is a schematic cross-section view of an acoustic sensor. FIG. 6D is a schematic perspective view of part of the acoustic sensor.

In the embodiment, a third strain sensing element S3 may be further provided, for example. The third strain sensing element is provided on the first surface F1a, for example. The third strain sensing element S3 includes a fifth magnetic layer 30b, a sixth magnetic layer 40b, and a third intermediate layer 35b provided between the fifth magnetic layer 30b and the sixth magnetic layer 40b.

FIG. 6D shows the third strain sensing element S3. The configuration and material described in regard to the first strain sensing element S1 may be used for the configuration, material, etc. of each layer included in the third strain sensing element S3, for example.

Figure 7:
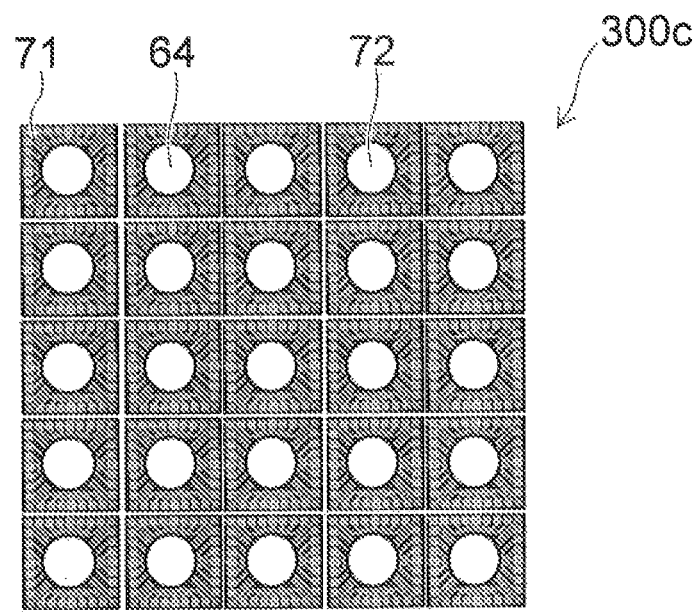
FIG. 7 is a schematic plan view illustrating part of an acoustic sensor according to the second embodiment.

FIG. 7 is a schematic plan view illustrating part of an acoustic sensor according to the second embodiment.

As shown in FIG. 7, a plurality of sensor units 72 are formed integrally on the base 70, for example. The composite base on which a plurality of sensor units 72 are formed integrally can be fabricated by using semiconductor technology.

The embodiment provides a high-sensitivity acoustic sensor.

Third Embodiment

Figure 8:
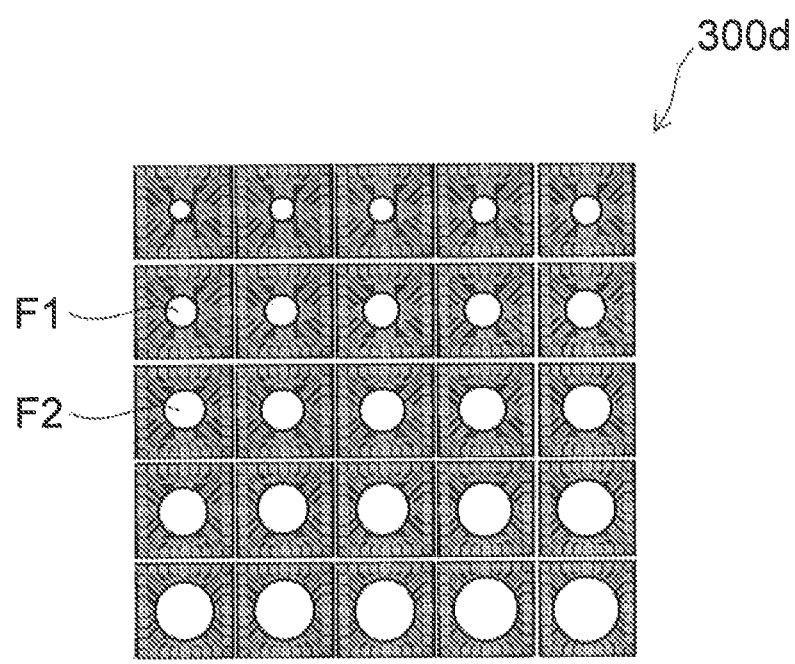
FIG. 8 is a schematic plan view illustrating an acoustic sensor according to a third embodiment.

FIG. 8 is a schematic plan view illustrating an acoustic sensor according to a third embodiment.

As shown in FIG. 8, also in an acoustic sensor 300d according to the embodiment, a plurality of sensor units 72 are provided. The plurality of sensor units 72 are formed integrally, for example. In this example, the sizes of the transducer thin films 64 included in the plurality of sensor units 72 are different from one another. Otherwise, the acoustic sensor 300d is similar to the acoustic sensor 300c.

In this example, the shape of the transducer thin film 64 is a circle. In the embodiment, the shape of the transducer thin film 64 is arbitrary.

The resonance frequency of the sensor unit 72 depends on the size and thickness of the transducer thin film 64. When the shape of the transducer thin film 64 is a circle, the resonance frequency of the sensor unit 72 depends on the diameter of the transducer thin film 64, for example.

The size of the strain sensing element 50 is not more than 1/50 of the size of the transducer thin film 64, for example. The influence of the strain sensing element (the size thereof) on the resonance frequency of the sensor unit is small.

In the acoustic sensor 300d, since the sizes of the plurality of transducer thin films 64 are different from one another, the resonance frequencies of the plurality of sensor units 72 are different from one another. Sensor units 72 having substantially equal resonance frequencies may be included among the plurality of sensor units 72.

That is, the acoustic sensor according to the embodiment (the acoustic sensor 300d) includes the base 70, the first strain sensing element S1, and the second strain sensing element S2. The base 70 includes the first film unit F1 and the second film unit F2. The second strain sensing element S2 is provided on the surface of the second film unit (the second surface). The area of the second surface and the area of the surface of the first film unit (the first surface F1a) are different.

Figure 9:
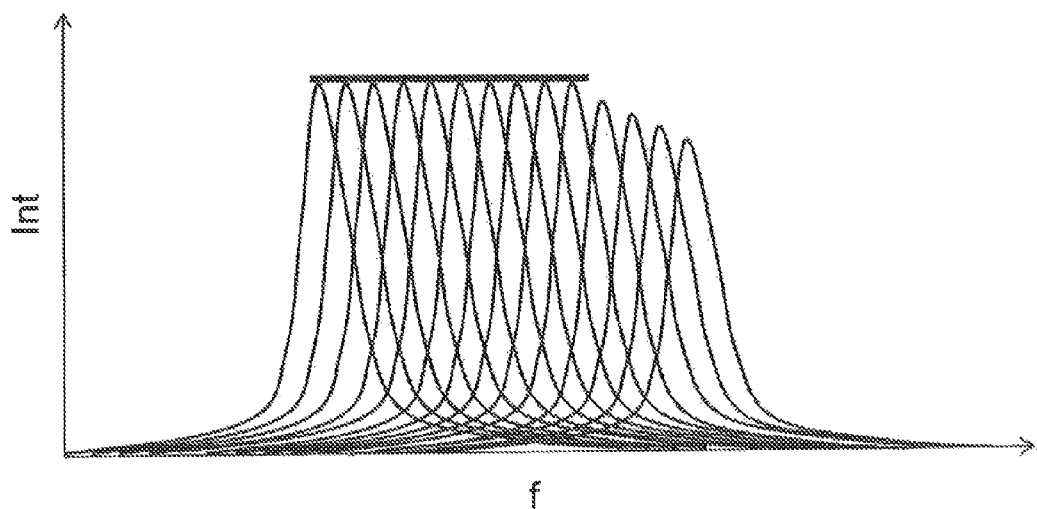
FIG. 9 is a schematic diagram showing characteristics of the acoustic sensor.
Figure 10A:
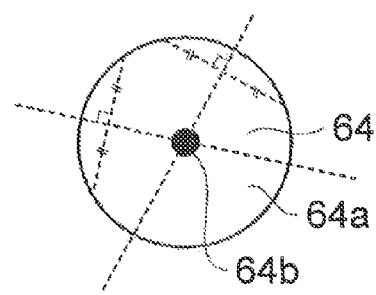
FIG. 10A to FIG. 10D are schematic plan views illustrating parts of acoustic sensors according to a fourth embodiment.
Figure 10B:
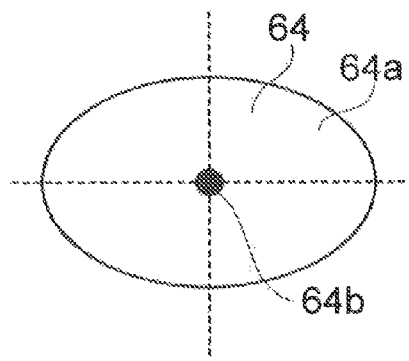
Figure 10C:
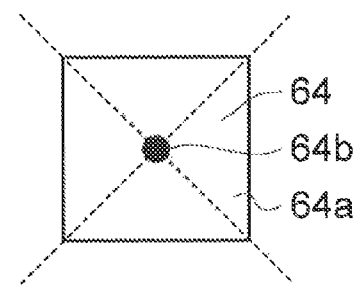
Figure 10D:
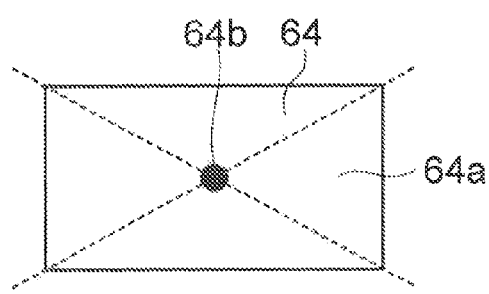

FIG. 9 is a schematic diagram showing characteristics of the acoustic sensor.

The horizontal axis of FIG. 9 is frequency f. The vertical axis is intensity int.

In the acoustic sensor, the band of the frequency characteristics in one sensor unit 72 is narrow. In this case, the sensitivity is high in the neighborhoods of resonance points.

In the acoustic sensor, a plurality of transducer thin films 64 are provided. The diameters or thicknesses of the plurality of transducer thin films 64 are different from one another, for example. Thereby, the band widths of the sensor units 72 overlap with one another. Such an array-type sensor can resonate in a wide frequency range. The frequency characteristics of such an array-type sensor are a wide band as a whole.

On the other hand, in the acoustic sensor of the reference example utilizing a piezoelectric material such as PZT, a damper (a sound absorber) is provided on the piezoelectric element, for example. The damper absorbs unnecessary vibration to suppress resonance, and the band is widened. However, the sensitivity of the acoustic sensor of the reference example like this is low. The sensitivity of the acoustic sensor according to the embodiment is higher by approximately 10 to 30 dB than the sensitivity of the acoustic sensor of the reference example like that, for example.

In the embodiment, each sensor unit 72 operates in the neighborhood of the resonance point, for example. Therefore, an acoustic sensor with high sensitivity and wide band characteristics is obtained.

The embodiment provides a high-sensitivity acoustic sensor.

Fourth Embodiment

FIG. 10A to FIG. 10D are schematic plan views illustrating parts of acoustic sensors according to a fourth embodiment.

As shown in FIG. 10A to FIG. 10D, the shape of the film surface 64a of the transducer thin film 64 (the shape of the first surface F1a) is a circle, a flat circle (including an ellipse), a square, a rectangle, or a polygon, for example. The shape of the film surface 64a may be a shape in which the corners of a polygon are rounded, for example. In this case, the centroid 64b of the film surface 64a is the center of the circle, the center of the flat circle, the center of the ellipse, the center of the diagonals of the square, or the center of the diagonals of the rectangle.

In the case of a circular transducer thin film 64, the diameter of the transducer thin film 64 determines the resonance frequency thereof predominantly, for example.

In a rectangular transducer thin film 64 having the same area as a circular transducer thin film 64, the length of the short side of the rectangle is shorter than the radius of the circle, for example. In this case, the length of the short side of the rectangular transducer thin film 64 determines the resonance frequency predominantly. That is, the resonance frequency of the rectangular transducer thin film 64 tends to be higher than the resonance frequency of the circular transducer thin film 64 with the same area.

The resonance frequency of the acoustic sensor can be set high by using the transducer thin film 64 with such a shape.

Also the embodiment provides a high-sensitivity acoustic sensor.

Fifth Embodiment

Figure 11A:
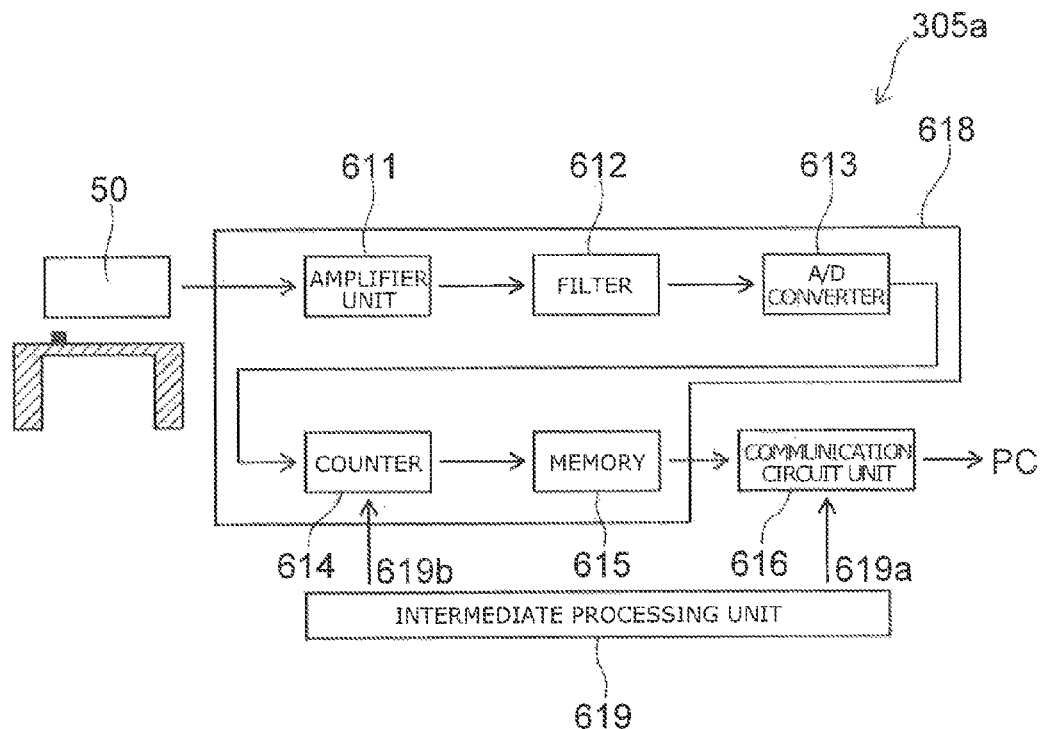
FIG. 11A and FIG. 11B are schematic diagrams illustrating acoustic sensors according to a fifth embodiment.
Figure 11B:
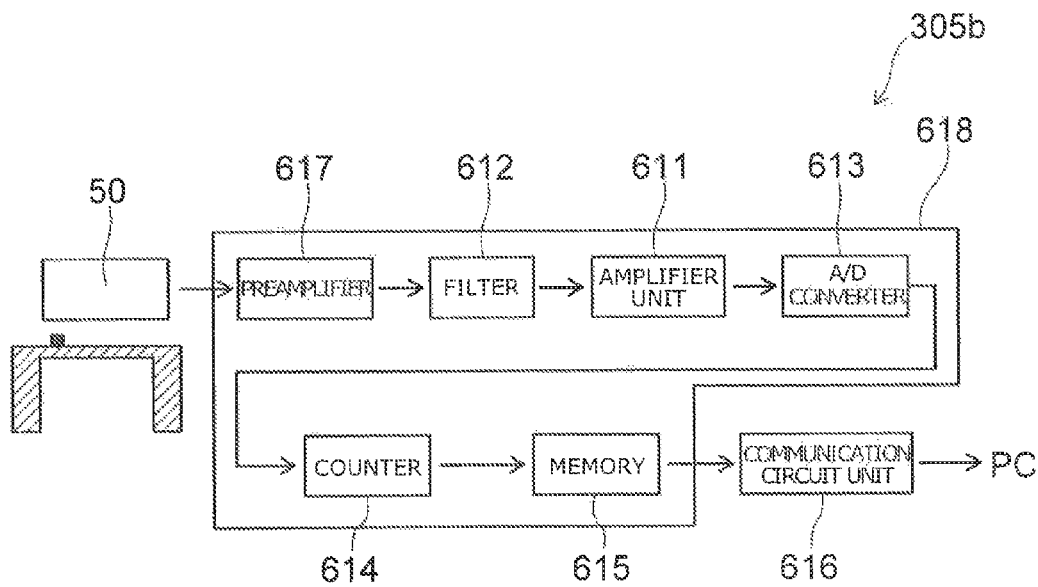

FIG. 11A and FIG. 11B are schematic diagrams illustrating acoustic sensors according to a fifth embodiment.

The drawings illustrate circuits included in acoustic sensors. These circuits may not be included in the acoustic sensors, and may be connected to the acoustic sensors.

As shown in FIG. 11A, an acoustic sensor 305a according to the embodiment includes an electronic circuit unit 618 and a communication circuit unit 616. The electronic circuit unit 618 and the communication circuit unit 616 are connected to each other. The electronic circuit unit 618 processes the ultrasonic signal detected by the strain sensing element 50. The communication circuit unit 616 transmits the data processed by the electronic circuit unit 618 to the outside. The electronic circuit unit 618 includes an amplifier unit 611, a filter 612, an A/D converter 613, a counter 614, and a memory 615, for example.

As shown in FIG. 11B, in an acoustic sensor 305b according to the embodiment, the electronic circuit unit 618 includes an amplifier unit 611, a filter 612, an A/D converter 613, a counter 614, a memory 615, and a preamplifier 617, for example.

The amplifier unit 611 amplifies a detected weak electric signal for subsequent processing. The filter 612 removes extraneous electric or magnetic noise. The filter 612 includes at least one of a low-pass filter and a high-pass filter. The A/D converter 613 converts an analog signal to a digital signal. The counter 614 counts the number of appearances of signals exceeding the prescribed threshold. The memory 615 stores the primary processed data. The amplifier unit 611 amplifies a detected small acoustic emission signal. In the amplification, amplification of 20 dB or more is made, for example.

External noise is likely to get mixed in the signal between the strain sensing element 50 and the amplifier unit 611. In the acoustic sensor 305a according to the embodiment, the amplifier unit 611 is provided inside. Therefore, the cable length between the strain sensing element 50 and the amplifier unit 611 is short, and the mixing-in of external noise is significantly suppressed between the strain sensing element 50 and the amplifier unit 611.

The filter 612 is a band-pass filter, for example. The filter 612 allows signals in the frequency range of the ultrasonic wave of the objective (for example, 20 kHz to 1 MHz) to pass through, and does not allow the signals of the other frequencies to pass through (for example, attenuates them), for example. Thereby, the waveforms other than the frequency band of the objective, such as background noise and white noise, are removed.

The cutting-off of the noise transmission path or shielding is made as a measure against other noise such as acoustic noise having frequency components close to acoustic emission and electric or magnetic noise, for example.

The analog ultrasonic signal is converted to a digital signal by the A/D converter 613.

The counter 614 counts the number of acoustic emission events. The number of acoustic emission events is the number of times in which the magnitude of the amplitude of the acoustic emission wave exceeds the predetermined threshold, for example.

In the acoustic emission wave detected, longitudinal waves, transverse waves, elastic surface waves, and reflected waves of these are mixed. After the generation of acoustic emission, the longitudinal waves arrive at the acoustic sensor first, and the transverse waves arrive next, for example. The elastic surface waves propagate on the surface of the measuring object. The number of acoustic emission events measured by the counter 614 is the cumulative number of detections of these acoustic emission waves, for example.

The memory 615 stores the primary data of the electronic circuit unit 618 in the acoustic sensor.

The communication circuit unit 616 performs the external communication of the primary processed data processed by the electronic circuit unit 618. The communication circuit unit 616 transmits data to a PC or the like serving as an intermediate processing unit, for example. The communication circuit unit 616 is connected to a connector and a cable in order to perform external communication.

In a user PC 619 (an intermediate processing unit), an output request 619a or threshold setting 619b is performed in regard to the acoustic sensor, for example.

Sixth Embodiment

Figure 12:
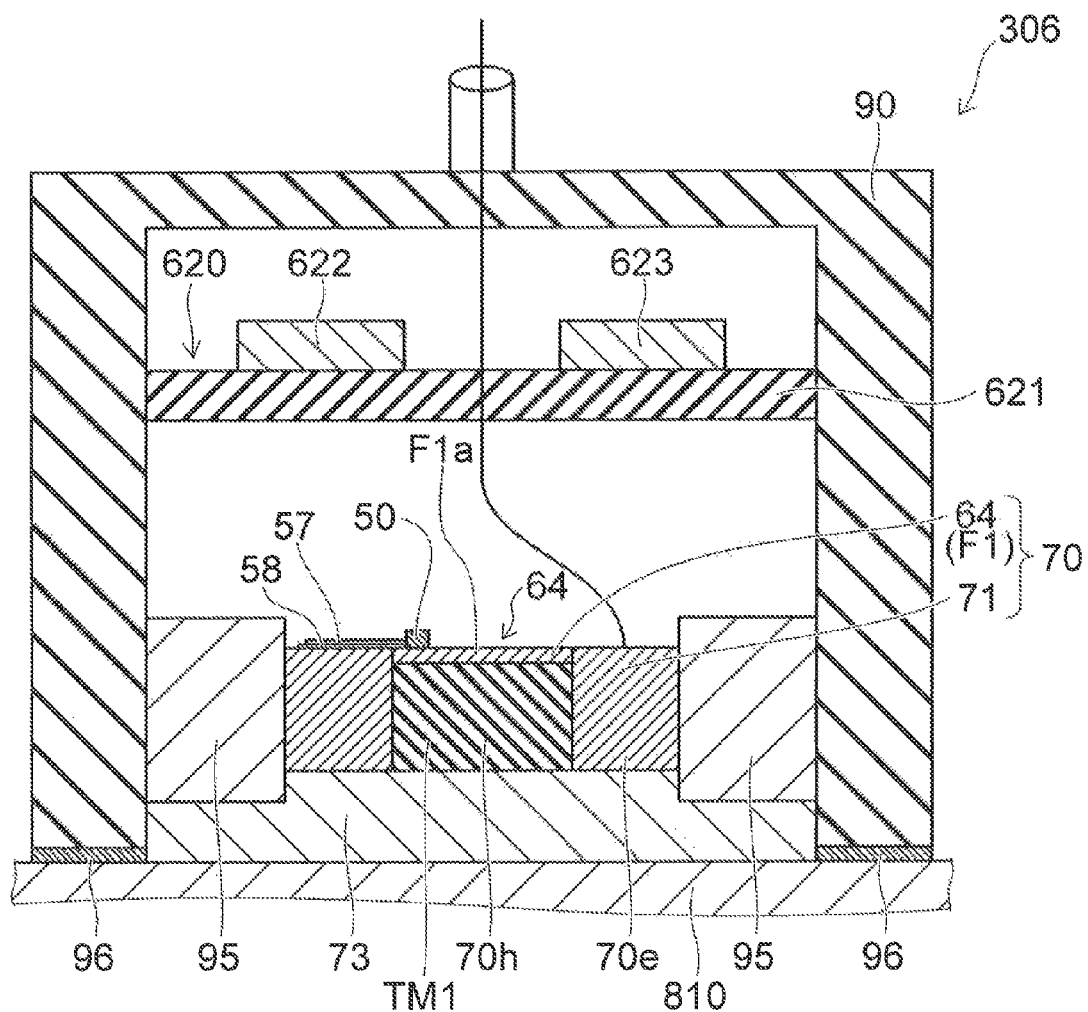
FIG. 12 is a schematic cross-sectional view illustrating an acoustic sensor according to a sixth embodiment.

FIG. 12 is a schematic cross-sectional view illustrating an acoustic sensor according to a sixth embodiment.

As shown in FIG. 12, an acoustic sensor 306 according to the embodiment includes a power receiving unit 620 in addition to any one of the acoustic sensors according to the first to fifth embodiments. The power receiving unit 620 is provided in the housing 90, for example. The power receiving unit 620 includes a power receiving unit substrate 621, and an amplifier 622 and a power transfer circuit 623 provided on the power receiving unit substrate 621, for example. The power receiving unit 620 forms a power receiving unit of ultrasonic wireless power supply, for example.

Figure 13:
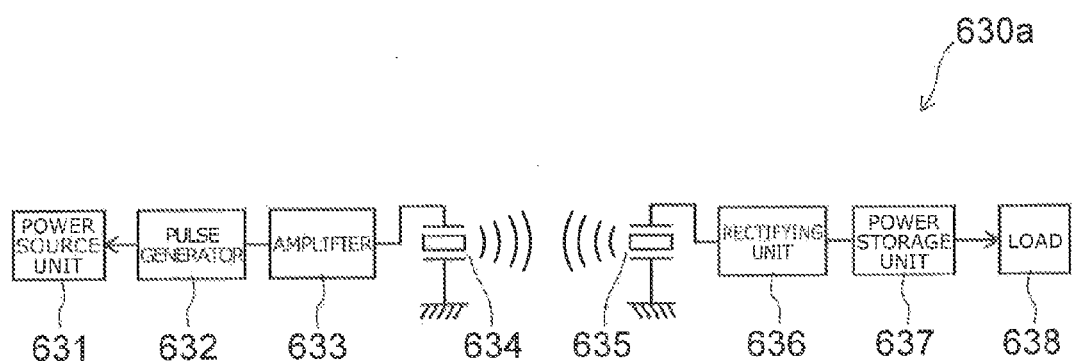
FIG. 13 is a schematic diagram illustrating an acoustic sensor according to the sixth embodiment.

FIG. 13 is a schematic diagram illustrating an acoustic sensor according to the sixth embodiment.

FIG. 13 illustrates a circuit unit used for an acoustic sensor 306a according to the embodiment. FIG. 13 illustrates a block diagram of a power transfer system using an ultrasonic wave as a transfer means. The wireless power transfer system based on an ultrasonic wave includes a power transfer unit 630a and a power receiving unit 630b.

The power transfer unit 630a transfers electric power. The power transfer unit 630a includes a power source unit 631, a pulse generator 632, an amplifier 633, and an ultrasonic transducer 634, for example. The pulse generator 632 generates an AC voltage pulse. The generated AC voltage pulse is amplified by the amplifier 633, and is applied to the ultrasonic transducer 634. Thereby, an ultrasonic wave is generated.

The power receiving unit 630b receives electric power. The power receiving unit 630b includes an ultrasonic transducer 635, a rectifying unit 636, a power storage unit 637, and a load 638 (an electronic circuit), for example. The power receiving unit 630b converts the received ultrasonic wave to DC power. Electric power is supplied to the load 638.

Figure 14:
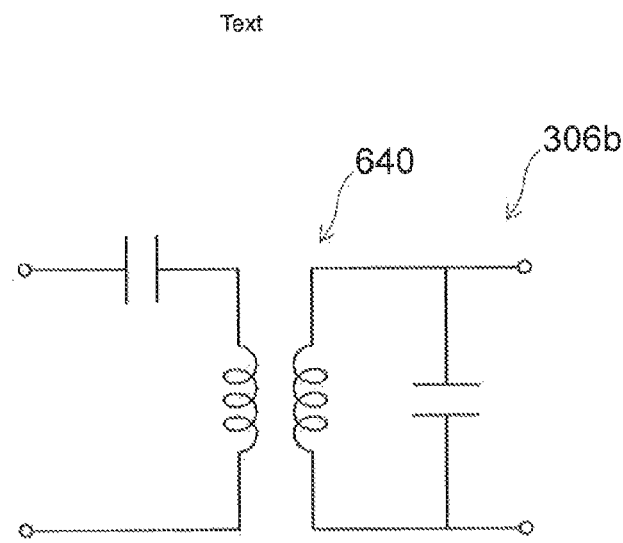
FIG. 14 is a schematic diagram illustrating an acoustic sensor according to the sixth embodiment.

FIG. 14 is a schematic diagram illustrating an acoustic sensor according to the sixth embodiment.

FIG. 14 illustrates a rectifying circuit 640 used for an acoustic sensor 306b according to the embodiment. The rectifying circuit 640 is a rectifying circuit for a wireless power transfer system. By the power receiving unit provided in the housing 90, electric power is supplied wirelessly without using a cable.

Seventh Embodiment

FIG. 15A to FIG. 15E are schematic cross-sectional views showing acoustic sensors according to a seventh embodiment.

Figure 15A:
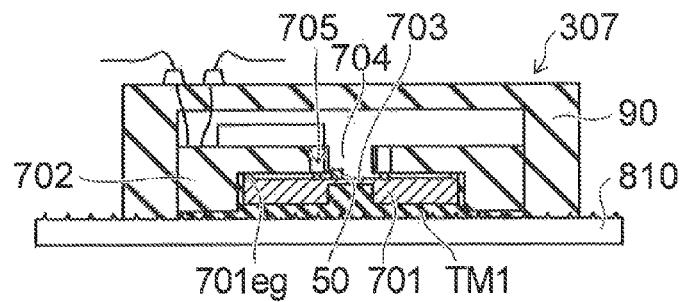
FIG. 15A to FIG. 15E are schematic cross-sectional views showing acoustic sensors according to a seventh embodiment.

As shown in FIG. 15A, in an acoustic sensor 307, a chip 701 and a printed circuit board 702 are provided. The chip 701 is attached to the printed circuit board 702 by an adhesive applied to an chip edge portion 701eg, for example.

The printed circuit board 702 is provided with a hole 704 in a position above a diaphragm 703, for example. Thereby, the diaphragm 703 can be deformed. The printed circuit board 702 includes a hole 705 for extracting an interconnection.

Figure 15B:
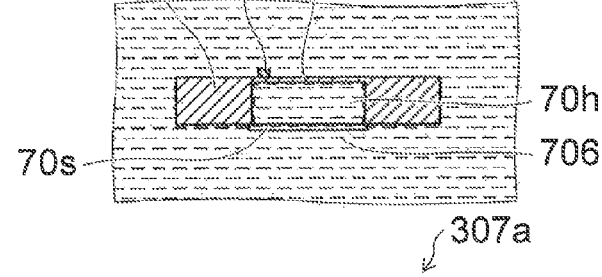

As shown in FIG. 15B, the filling of a liquid 706 into the hollow portion 70h is performed in the liquid 706, for example. After the liquid filling, the liquid may be sealed with a photocurable resin 70s or the like, for example. If the liquid injection into the hollow portion 70h is performed in the air, a difference may occur between the pressure applied to the upper surface of the diaphragm 703 and the pressure applied to the lower surface, and the diaphragm 703 may be warped. The warpage of the diaphragm can be suppressed by putting the liquid 706 into the hollow portion 70h in the liquid 706. The chip 701 is treated with waterproof coating, for example.

Figure 15C:
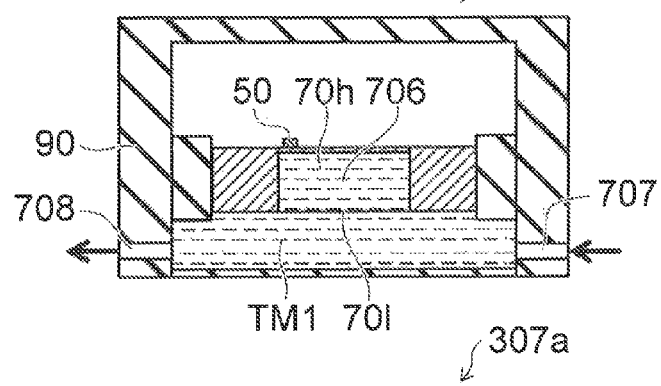

As shown in FIG. 15C, in an acoustic sensor 307a, the housing 90 is provided with an injection hole 707 and a vent hole 708. In this example, the injection hole 707 and the vent hole 708 are provided at the side surface of the housing 90.

The liquid 706 is injected into the hollow portion 70h, and the lower surface 701 of the liquid 706 is flat, for example. After that, a liquid is injected through the injection hole 707. At this time, the liquid is put in while the gas is removed through the vent hole 708. Thereby, the liquid can be put in with no gas left, for example. After the liquid is put in, the injection hole 707 and the vent hole 708 are sealed. A photocurable resin is used for the sealing of the injection hole 707 and the vent hole 708, for example.

Figure 15D:
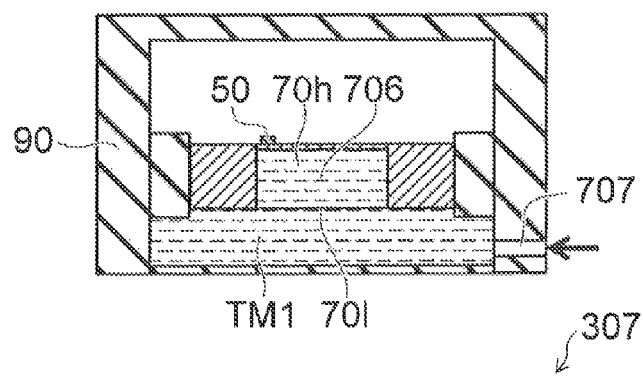

As shown in FIG. 15D, the vent hole 708 may not be provided. The space surrounded by the housing and the base is sealed by atmospheric pressure. In this case, after the acoustic sensor is decompressed, the injection hole 707 is immersed in the liquid 706. After that, the acoustic sensor is returned to atmospheric pressure to cause a difference in atmosphere, and consequently the liquid 706 enters the hollow portion 70h in the housing 90. Although the diaphragm is bent downward during decompression, it returns to its original position when returned to atmospheric pressure. Finally, the injection hole 707 is sealed. A photocurable resin is used for the sealing of the injection hole 707, for example. In the acoustic sensor according to the embodiment, by using such a method for liquid filling, a liquid can be put in without generating a strain on the diaphragm after the liquid filling.

Figure 15E:
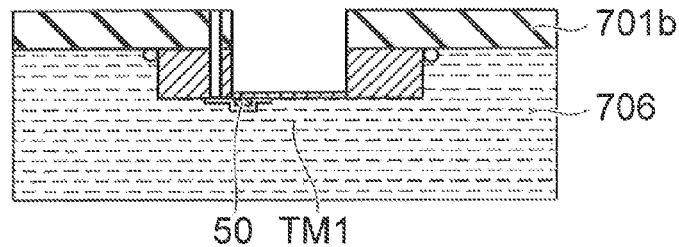

As shown in FIG. 15E, in an acoustic sensor 307b, the liquid 706 is disposed under a chip 701b. The strain sensing element 50 may come into contact with the surrounding liquid 706 and a short circuit may be formed. The strain sensing element 50 is treated with waterproof coating, for example.

The diameter of the diaphragm is not less than 1 μm and not more than 3 mm, for example. It is preferably not less than 60 μm and not more than 1 mm. The diameter of the strain sensing element 50 is 20 μm, for example. Therefore, the influence of the waterproof coating of the strain sensing element 50 on the strain of the diaphragm 703 is small.

Figure 16:
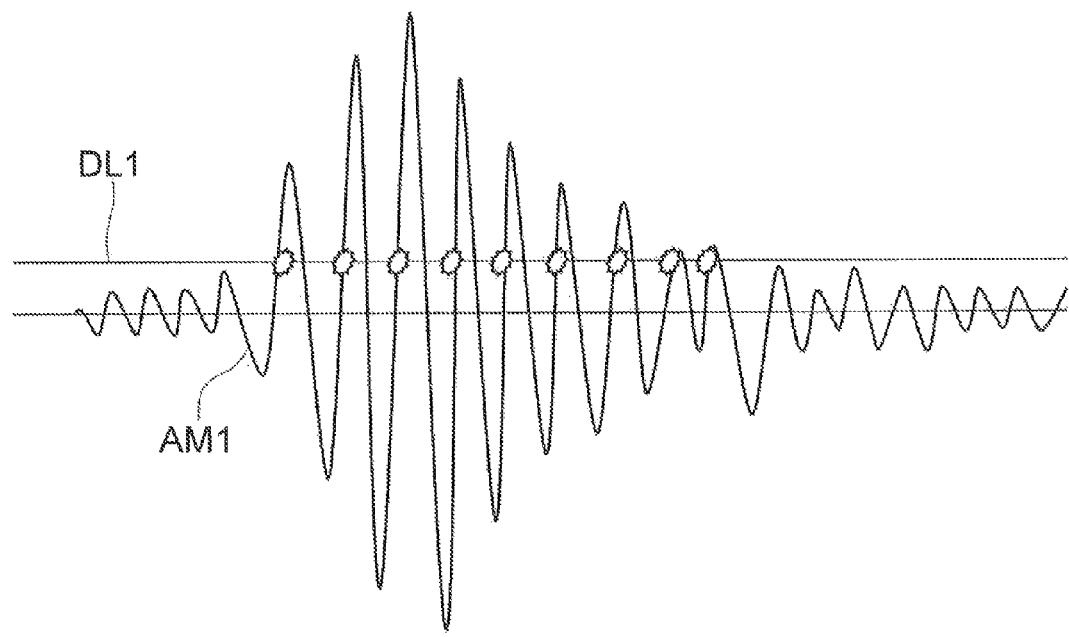
FIG. 16 is a schematic diagram showing an acoustic emission wave.

FIG. 16 is a schematic diagram showing an acoustic emission wave.

As a break of the measuring object 810 comes closer, the frequency of occurrence of acoustic emission becomes higher, for example. The degree of degradation of the measuring object 810 is estimated by measuring the occurrence of acoustic emission. As shown in FIG. 16, the number of times in which the amplitude waveform AM1 of the acoustic emission wave exceeds the prescribed value DL1 is measured.

Eighth Embodiment

Figure 17:
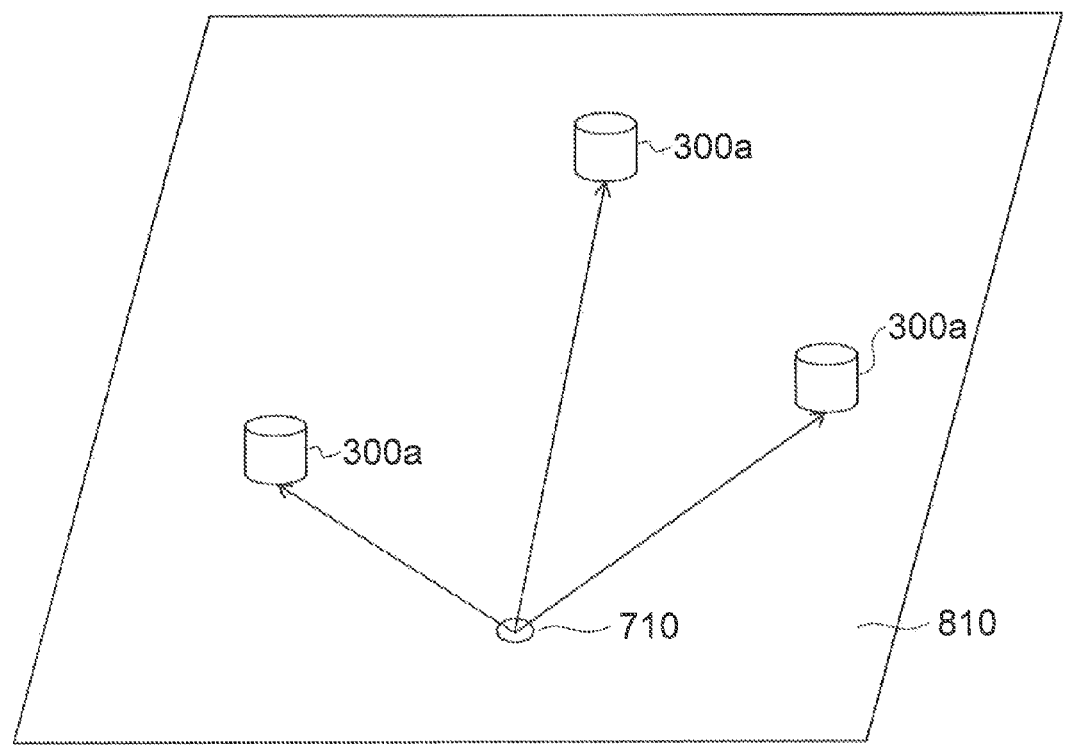
FIG. 17 is a schematic diagram illustrating an acoustic sensor system according to an eighth embodiment.

FIG. 17 is a schematic diagram illustrating an acoustic sensor system according to an eighth embodiment.

As shown in FIG. 17, in an acoustic sensor system 350 according to the embodiment, a plurality of acoustic sensors are used. In this example, a plurality of acoustic sensors 300a are used. As the acoustic sensor, any acoustic sensor according to the embodiments described above and modifications thereof may be used. By the plurality of acoustic sensors, the accuracy of position identification (position location) of an acoustic emission generation source 710 is improved, for example. The interval of installation of acoustic sensors is set narrower than the propagation distance of acoustic emission in the measuring object 810, for example. A plurality of acoustic sensors 300a are arranged on a straight line, for example. Thereby, the one-dimensional position of the acoustic emission generation source 710 can be identified, for example. A plurality of acoustic sensors 300a are arranged on the same plane, for example. Thereby, the two-dimensional position of the acoustic emission generation source 710 can be identified, for example. A plurality of acoustic sensors 300a are arranged on a plurality of planes, for example. Thereby, the three-dimensional position of the acoustic generation source 710 can be identified, for example.

The embodiment provides an acoustic sensor and an acoustic sensor system.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, embodiments of the invention are described with reference to specific examples. However, the embodiment of the invention is not limited to these specific examples. For example, one skilled in the art may appropriately select specific configurations of components of acoustic sensors and acoustic sensor systems such as bases, sensor units, film units, transducer thin films, fixing units, strain sensing elements, magnetic layers, intermediate layers, transmitting materials, acoustic matching layers, and signal processing circuits from known art and similarly practice the invention. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all acoustic sensors and acoustic sensor systems practicable by an appropriate design modification by one skilled in the art based on the acoustic sensors and the acoustic sensor systems described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. An acoustic sensor comprising:
a base including a support and a first film unit supported by the support, the first film unit being flexible; and
a first strain sensing element provided on a first surface of the first film unit, the first strain sensing element including a first magnetic layer, a second magnetic layer, and a first intermediate layer provided between the first magnetic layer and the second magnetic layer, an acoustic wave being transmitted to the first film unit via a first transmitting material, the first transmitting material being in contact with the first film unit, an electric resistance between the first magnetic layer and the second magnetic layer being variable in accordance with the acoustic wave.

2. The acoustic sensor according to claim 1, wherein the first transmitting material is disposed in a space partitioned by the support and the first film unit.

3. The acoustic sensor according to claim 1, further comprising a fixing unit to fix the base to a measuring object, the measuring object emitting an acoustic wave, an acoustic impedance of the first transmitting material being lower than an acoustic impedance of the measuring object.

4. The acoustic sensor according to claim 1, further comprising:
a coupler material member;
a housing; and
a bottom plate,
wherein the base, the first strain sensing element, and the first transmitting material are provided in the housing,
wherein the first transmitting material is disposed between the bottom plate and the first film unit,
wherein the bottom plate is provided between the coupler material member and the first transmitting material, and
wherein the coupler material member includes at least one of an epoxy-based adhesive, wax, grease, or a silicone compound.

5. The acoustic sensor according to claim 4, further comprising an acoustic coupler material provided between the bottom plate and a measuring object.

6. The acoustic sensor according to claim 1, wherein the first transmitting material includes at least one of a liquid, a gel, and a solid.

7. The acoustic sensor according to claim 1, wherein the first transmitting material includes at least one of water, glycerin, mercury, and rubber.

8. The acoustic sensor according to claim 1, wherein the first transmitting material includes:
a first layer; and
a second layer provided between the first layer and the first film unit,
the first layer including a solid, and the second layer including at least one of a liquid or a gel.

9. The acoustic sensor according to claim 1, further comprising:
a second strain sensing element; and
a second transmitting material,
the base further including a second film unit supported by the support,
the second strain sensing element being provided on a second surface of the second film unit, the second strain sensing element including a third magnetic layer, a fourth magnetic layer, and a second intermediate layer provided between the third magnetic layer and the fourth magnetic layer, the second transmitting material being in contact with the second film unit and configured to transmit the acoustic wave to the second film unit.

10. The acoustic sensor according to claim 9, wherein an area of the first surface is different from an area of the second surface.

11. The acoustic sensor according to claim 9, wherein a resonance frequency of the first strain sensing element is different from a resonance frequency of the second strain sensing element.

12. The acoustic sensor according to claim 1, further comprising a second strain sensing element, the second strain sensing element being provided on the first surface, the second strain sensing element including a third magnetic layer, a fourth magnetic layer, and a second intermediate layer provided between the third magnetic layer and the fourth magnetic layer.

13. The acoustic sensor according to claim 9, further comprising a third strain sensing element, the third strain sensing element being provided on the first surface, the third strain sensing element including a fifth magnetic layer, a sixth magnetic layer, and a third intermediate layer provided between the fifth magnetic layer and the sixth magnetic layer.

14. The acoustic sensor according to claim 1, wherein a shape of the first surface is a circle.

15. The acoustic sensor according to claim 1, wherein a shape of the first surface is a polygon.

16. The acoustic sensor according to claim 1, wherein a shape of the first surface is a rectangle.

17. The acoustic sensor according to claim 1, wherein the first surface has rounded corners.

18. The acoustic sensor according to claim 1, wherein
the first strain sensing element has a first area when projected onto the first surface, and the first area is not more than $1/5$ of an area of the first surface.

19. An acoustic sensor system comprising the acoustic sensor according to claim 1 provided in a plurality.

20. An acoustic sensor comprising:
a base including a support and a first film unit supported by the support, the first film unit being flexible;
a first strain sensing element provided on a first surface of the first film unit, the first strain sensing element including a first magnetic layer, a second magnetic layer, and a first intermediate layer provided between the first magnetic layer and the second magnetic layer; and
a first transmitting material in contact with the first film unit and configured to transmit an acoustic wave to the first film unit.

21. The acoustic sensor according to claim 1, wherein an angle between a magnetization of the first magnetic layer and a magnetization of the second magnetic layer is variable in accordance with the acoustic wave.

22. The acoustic sensor according to claim 1, wherein the first transmitting material includes:
a first layer; and
a second layer provided between the first layer and the first film unit, the first layer including a gel, and the second layer including a liquid.

23. The acoustic sensor according to claim 20, wherein an electric resistance between the first magnetic layer and the second magnetic layer varies in accordance with the acoustic wave.

24. The acoustic sensor according to claim 20, further comprising:
a coupler material member;
a housing; and
a bottom plate,
wherein the base, the first strain sensing element, and the first transmitting material are provided in the housing,
wherein the first transmitting material are disposed between the bottom plate and the first film unit,
wherein the bottom plate is provided between the coupler material member and the first transmitting material,
wherein the coupler material member includes at least one of an epoxy-based adhesive, wax, grease, or a silicone compound.

25. The acoustic sensor according to claim 20, wherein the first transmitting material includes:
a first layer; and
a second layer provided between the first layer and the first film unit,
the first layer including a solid, and the second layer including at least one of a liquid or a gel.

26. The acoustic sensor according to claim 20, wherein the first transmitting material includes:
a first layer; and
a second layer provided between the first layer and the first film unit, the first layer including a gel, and the second layer including a liquid.

* * * * *